United States Patent
Dunn

(10) Patent No.: US 10,405,861 B2
(45) Date of Patent: Sep. 10, 2019

(54) NEGATIVE PRESSURE WOUND CLOSURE DEVICE

(71) Applicant: University of Massachusetts, Boston, MA (US)

(72) Inventor: Raymond Dunn, Shrewsbury, MA (US)

(73) Assignee: University of Massachusetts, Boston, MA (US)

(*) Notice: Subject to any disclaimer, the term of this patent is extended or adjusted under 35 U.S.C. 154(b) by 301 days.

(21) Appl. No.: 15/083,675

(22) Filed: Mar. 29, 2016

(65) Prior Publication Data

US 2016/0278773 A1  Sep. 29, 2016

Related U.S. Application Data

(60) Continuation of application No. 14/581,685, filed on Dec. 23, 2014, now Pat. No. 9,301,742, which is a
(Continued)

(51) Int. Cl.
*A61M 35/00* (2006.01)
*A61M 1/00* (2006.01)
(Continued)

(52) U.S. Cl.
CPC .......... *A61B 17/08* (2013.01); *A61B 17/0057* (2013.01); *A61F 13/00068* (2013.01); *A61M 1/008* (2013.01); *A61M 1/0088* (2013.01); *A61B 2017/00561* (2013.01); *A61B 2017/00654* (2013.01); *A61B 2017/081* (2013.01);
(Continued)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS

| 3,194,239 A | 7/1965 | Sullivan |
| 3,789,851 A | 2/1974 | LeVeen |

(Continued)

FOREIGN PATENT DOCUMENTS

| CN | 1438904 | 8/2003 |
| CN | 101112326 A | 1/2008 |

(Continued)

OTHER PUBLICATIONS

Hougaard, et al., "The open abdomen: temporary closure with a modified negative pressure therapy technique", International Wound Journal, (2014), ISSN 1742-4801, pp. 13-16.
(Continued)

*Primary Examiner* — Tatyana Zalukaeva
*Assistant Examiner* — Ilya Y Treyger
(74) *Attorney, Agent, or Firm* — McCarter & English, LLP; Thomas O. Hoover

(57) ABSTRACT

The present invention relates to a negative pressure wound closure system and methods for using such a system. Preferred embodiments of the invention facilitate closure of the wound by preferentially contracting to provide for movement of the tissue. Preferred embodiments can utilize tissue grasping elements to apply a wound closing force to the tissue.

68 Claims, 13 Drawing Sheets

Related U.S. Application Data division of application No. 13/365,615, filed on Feb. 3, 2012, now Pat. No. 9,226,737.

(60) Provisional application No. 61/439,525, filed on Feb. 4, 2011.

(51) Int. Cl.

| | | |
|---|---|---|
| *A61F 13/00* | (2006.01) | |
| *A61B 17/08* | (2006.01) | |
| *A61B 17/00* | (2006.01) | |
| *A61M 27/00* | (2006.01) | |
| *A61F 13/02* | (2006.01) | |

(52) U.S. Cl.
CPC ........... *A61F 2013/0054* (2013.01); *A61F 2013/00174* (2013.01); *A61F 2013/00536* (2013.01); *A61F 2013/00544* (2013.01); *A61F 2013/00548* (2013.01)

(56) References Cited

U.S. PATENT DOCUMENTS

| | | | |
|---|---|---|---|
| 4,467,805 | A | 8/1984 | Fukuda |
| 4,699,134 | A | 10/1987 | Samuelsen |
| 4,815,468 | A | 3/1989 | Annand |
| 5,264,218 | A | 11/1993 | Rogozinski |
| 5,409,472 | A | 4/1995 | Rawlings et al. |
| 5,415,715 | A | 5/1995 | Delage et al. |
| 5,423,857 | A | 6/1995 | Rosenman et al. |
| 5,512,041 | A | 4/1996 | Bogart |
| 5,584,859 | A | 12/1996 | Brotz |
| 5,636,643 | A | 6/1997 | Argenta et al. |
| 5,695,777 | A | 12/1997 | Donovan et al. |
| 5,960,497 | A | 10/1999 | Castellino et al. |
| 6,080,168 | A | 6/2000 | Levin et al. |
| 6,086,591 | A | 7/2000 | Bojarski |
| 6,142,982 | A | 11/2000 | Hunt et al. |
| 6,176,868 | B1 | 1/2001 | Detour |
| 6,548,727 | B1 | 4/2003 | Swenson |
| 6,553,998 | B2 | 4/2003 | Heaton et al. |
| 6,566,575 | B1 | 5/2003 | Stickels et al. |
| 6,685,681 | B2 | 2/2004 | Lockwood et al. |
| 6,695,823 | B1 | 2/2004 | Lina et al. |
| 6,712,830 | B2 | 3/2004 | Esplin |
| 6,767,334 | B1 | 7/2004 | Randolph |
| 6,770,794 | B2 | 8/2004 | Fleischmann |
| 6,787,682 | B2 | 9/2004 | Gilman |
| 6,814,079 | B2 | 11/2004 | Heaton et al. |
| 6,893,452 | B2 | 5/2005 | Jacobs |
| 6,936,037 | B2 | 8/2005 | Bubb |
| 6,951,553 | B2 | 10/2005 | Bubb et al. |
| 6,977,323 | B1 | 12/2005 | Swenson |
| 6,994,702 | B1 | 2/2006 | Johnson |
| 7,004,915 | B2 | 2/2006 | Boynton et al. |
| 7,025,755 | B2 | 4/2006 | Epstein |
| 7,070,584 | B2 | 7/2006 | Johnson et al. |
| 7,117,869 | B2 | 10/2006 | Heaton et al. |
| 7,128,735 | B2 | 10/2006 | Weston |
| 7,144,390 | B1 | 12/2006 | Hannigan et al. |
| 7,153,312 | B1 | 12/2006 | Torrie et al. |
| 7,156,862 | B2 | 1/2007 | Jacobs et al. |
| 7,172,615 | B2 | 2/2007 | Morriss et al. |
| 7,189,238 | B2 | 3/2007 | Lombardo et al. |
| 7,196,054 | B1 | 3/2007 | Drohan et al. |
| 7,198,046 | B1 | 4/2007 | Argenta et al. |
| 7,216,651 | B2 | 5/2007 | Argenta et al. |
| D544,092 | S | 6/2007 | Lewis |
| 7,262,174 | B2 | 8/2007 | Jiang et al. |
| 7,279,612 | B1 | 10/2007 | Heaton et al. |
| 7,315,183 | B2 | 1/2008 | Hinterscher |
| 7,351,250 | B2 | 4/2008 | Zamierowski |
| 7,361,184 | B2 | 4/2008 | Joshi |
| 7,367,342 | B2 | 5/2008 | Butler |
| 7,381,211 | B2 | 6/2008 | Zamierowski |
| 7,381,859 | B2 | 6/2008 | Hunt et al. |
| 7,413,571 | B2 | 8/2008 | Zamierowski |
| 7,438,705 | B2 | 10/2008 | Karpowicz et al. |
| 7,494,482 | B2 | 2/2009 | Orgill et al. |
| 7,534,240 | B1 | 5/2009 | Johnson |
| 7,540,848 | B2 | 6/2009 | Hannigan et al. |
| 7,553,306 | B1 | 6/2009 | Hunt et al. |
| 7,553,923 | B2 | 6/2009 | Williams et al. |
| 7,569,742 | B2 | 8/2009 | Haggstrom et al. |
| 7,578,532 | B2 | 8/2009 | Schiebler |
| D602,583 | S | 10/2009 | Pidgeon et al. |
| 7,611,500 | B1 | 11/2009 | Lina et al. |
| 7,615,036 | B2 | 11/2009 | Joshi et al. |
| 7,618,382 | B2 | 11/2009 | Vogel et al. |
| 7,625,362 | B2 | 12/2009 | Boehringer et al. |
| 7,645,269 | B2 | 1/2010 | Zamierowski |
| 7,651,484 | B2 | 1/2010 | Heaton et al. |
| 7,670,323 | B2 | 3/2010 | Hunt et al. |
| 7,678,102 | B1 | 3/2010 | Heaton |
| 7,683,667 | B2 | 3/2010 | Kim |
| 7,699,823 | B2 | 4/2010 | Haggstrom et al. |
| 7,699,830 | B2 | 4/2010 | Martin |
| 7,699,831 | B2 | 4/2010 | Bengtson et al. |
| 7,700,819 | B2 | 4/2010 | Ambrosio et al. |
| 7,708,724 | B2 | 5/2010 | Weston |
| 7,713,743 | B2 | 5/2010 | Villanueva et al. |
| 7,722,528 | B2 | 5/2010 | Arnal et al. |
| 7,723,560 | B2 | 5/2010 | Lockwood et al. |
| 7,754,937 | B2 | 7/2010 | Boehringer et al. |
| 7,776,028 | B2 | 8/2010 | Miller et al. |
| 7,777,522 | B2 | 8/2010 | Yang |
| 7,779,625 | B2 | 8/2010 | Joshi et al. |
| D625,801 | S | 10/2010 | Pidgeon et al. |
| 7,815,616 | B2 | 10/2010 | Boehringer et al. |
| 7,820,453 | B2 | 10/2010 | Heylen et al. |
| 7,846,141 | B2 | 12/2010 | Weston |
| 7,857,806 | B2 | 12/2010 | Karpowicz et al. |
| 7,896,856 | B2 | 3/2011 | Petrosenko et al. |
| 7,909,805 | B2 | 3/2011 | Weston |
| 7,931,774 | B2 | 4/2011 | Hall et al. |
| 7,942,866 | B2 | 5/2011 | Radl et al. |
| 7,951,124 | B2 | 5/2011 | Boehringer et al. |
| 7,964,766 | B2 | 6/2011 | Blott et al. |
| 7,976,519 | B2 | 7/2011 | Bubb et al. |
| 7,976,524 | B2 | 7/2011 | Kudo et al. |
| 7,981,098 | B2 | 7/2011 | Boehringer et al. |
| 8,030,534 | B2 | 10/2011 | Radl et al. |
| 8,057,447 | B2 | 11/2011 | Olson et al. |
| 8,062,272 | B2 | 11/2011 | Weston |
| 8,062,295 | B2 | 11/2011 | McDevitt et al. |
| 8,062,331 | B2 | 11/2011 | Zamierowski |
| 8,070,773 | B2 | 12/2011 | Zamierowski |
| 8,080,702 | B2 | 12/2011 | Blott et al. |
| 8,100,887 | B2 | 1/2012 | Weston et al. |
| 8,114,126 | B2 | 2/2012 | Heaton et al. |
| 8,123,781 | B2 | 2/2012 | Zamierowski |
| 8,128,615 | B2 | 3/2012 | Blott et al. |
| 8,129,580 | B2 | 3/2012 | Wilkes et al. |
| 8,142,419 | B2 | 3/2012 | Heaton et al. |
| 8,162,909 | B2 | 4/2012 | Blott et al. |
| 8,172,816 | B2 | 5/2012 | Kazala, Jr. et al. |
| 8,182,413 | B2 | 5/2012 | Browning |
| 8,187,237 | B2 | 5/2012 | Seegert |
| 8,188,331 | B2 | 5/2012 | Barta et al. |
| 8,197,467 | B2 | 6/2012 | Heaton et al. |
| 8,207,392 | B2 | 6/2012 | Haggstrom et al. |
| 8,235,955 | B2 | 8/2012 | Blott et al. |
| 8,246,590 | B2 | 8/2012 | Hu et al. |
| 8,257,328 | B2 | 9/2012 | Augustine et al. |
| 8,273,105 | B2 | 9/2012 | Cohen et al. |
| 8,353,931 | B2 | 1/2013 | Stopek et al. |
| 8,357,131 | B2 | 1/2013 | Olson |
| 8,376,972 | B2 | 2/2013 | Fleischmann |
| 8,399,730 | B2 | 3/2013 | Kazala, Jr. et al. |
| 8,444,392 | B2 | 5/2013 | Turner et al. |
| 8,447,375 | B2 | 5/2013 | Shuler |
| 8,454,990 | B2 | 6/2013 | Canada et al. |
| 8,460,255 | B2 | 6/2013 | Joshi et al. |
| 8,460,257 | B2 | 6/2013 | Locke et al. |

(56) References Cited

U.S. PATENT DOCUMENTS

| | | |
|---|---|---|
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,562,576 B2 | 10/2013 | Hu et al. |
| 8,608,776 B2 | 12/2013 | Coward et al. |
| 8,622,981 B2 | 1/2014 | Hartwell et al. |
| 8,628,505 B2 | 1/2014 | Weston |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,715,256 B2 | 5/2014 | Greener |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,882,730 B2 | 11/2014 | Dmitry |
| 8,936,618 B2 | 1/2015 | Sealy et al. |
| 8,945,030 B2 | 2/2015 | Weston |
| 8,951,235 B2 | 2/2015 | Allen et al. |
| 9,050,398 B2 | 6/2015 | Armstrong et al. |
| 9,061,095 B2 | 6/2015 | Adie et al. |
| 9,084,845 B2 | 7/2015 | Adie et al. |
| 9,180,231 B2 | 11/2015 | Greener |
| 9,220,822 B2 | 12/2015 | Hartwell et al. |
| 9,226,737 B2 | 1/2016 | Dunn |
| 9,301,742 B2 | 4/2016 | Dunn |
| 9,408,755 B2 | 8/2016 | Larsson et al. |
| 9,421,132 B2 | 8/2016 | Dunn |
| 9,770,368 B2 | 9/2017 | Robinson et al. |
| 9,801,986 B2 | 10/2017 | Greener |
| 9,844,472 B2 | 12/2017 | Hammond et al. |
| 2001/0029956 A1 | 10/2001 | Argenta |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0108587 A1 | 6/2003 | Orgill et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0220660 A1 | 11/2003 | Kortanbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0243073 A1 | 12/2004 | Lockwood et al. |
| 2004/0267312 A1 | 12/2004 | Kanner et al. |
| 2005/0119694 A1 | 6/2005 | Jacobs et al. |
| 2005/0142331 A1 | 6/2005 | Anderson et al. |
| 2005/0182445 A1 | 8/2005 | Zamierowski |
| 2005/0209574 A1* | 9/2005 | Boehringer ............ A61F 13/36 604/289 |
| 2005/0222613 A1 | 10/2005 | Ryan |
| 2005/0258887 A1 | 11/2005 | Ito |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0027414 A1 | 2/2007 | Hoffman et al. |
| 2007/0032755 A1 | 2/2007 | Walsh |
| 2007/0032763 A1 | 2/2007 | Vogel |
| 2007/0038172 A1 | 2/2007 | Zamierowski |
| 2007/0052144 A1 | 3/2007 | Knirck et al. |
| 2007/0055209 A1 | 3/2007 | Patel et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0219513 A1 | 9/2007 | Lina et al. |
| 2007/0265585 A1 | 11/2007 | Joshi et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0108977 A1 | 5/2008 | Heaton et al. |
| 2008/0167593 A1 | 7/2008 | Fleischmann |
| 2008/0177253 A1 | 7/2008 | Boehringer et al. |
| 2008/0275409 A1 | 11/2008 | Kane et al. |
| 2008/0287973 A1 | 11/2008 | Aster et al. |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0227938 A1 | 9/2009 | Fasching et al. |
| 2009/0246238 A1 | 10/2009 | Gorman et al. |
| 2009/0259203 A1 | 10/2009 | Hu et al. |
| 2009/0299303 A1 | 12/2009 | Seegert |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0047324 A1 | 2/2010 | Fritz et al. |
| 2010/0081983 A1 | 4/2010 | Zocher et al. |
| 2010/0100022 A1 | 4/2010 | Greener et al. |
| 2010/0100063 A1 | 4/2010 | Joshi et al. |
| 2010/0106184 A1 | 4/2010 | Coward et al. |
| 2010/0121286 A1 | 5/2010 | Locke et al. |
| 2010/0121287 A1 | 5/2010 | Smith et al. |
| 2010/0125233 A1 | 5/2010 | Griffey et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160876 A1 | 6/2010 | Robinson et al. |
| 2010/0160901 A1 | 6/2010 | Hu et al. |
| 2010/0179515 A1 | 7/2010 | Swain et al. |
| 2010/0087854 A1 | 8/2010 | Stopek et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262126 A1 | 10/2010 | Hu et al. |
| 2010/0280468 A1 | 11/2010 | Haggstrom et al. |
| 2010/0292717 A1 | 11/2010 | Petier-Puchner et al. |
| 2010/0305490 A1 | 12/2010 | Coulthard et al. |
| 2010/0318046 A1 | 12/2010 | Boehringer et al. |
| 2011/0004173 A1 | 1/2011 | Hu et al. |
| 2011/0009838 A1 | 1/2011 | Greener |
| 2011/0015594 A1 | 1/2011 | Hu et al. |

(56) References Cited

U.S. PATENT DOCUMENTS

| | | |
|---|---|---|
| 2011/0021965 A1 | 1/2011 | Karp et al. |
| 2011/0022082 A1 | 1/2011 | Burke et al. |
| 2011/0054283 A1 | 3/2011 | Shuler |
| 2011/0054365 A1 | 3/2011 | Greener |
| 2011/0060204 A1 | 3/2011 | Weston |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0130774 A1 | 6/2011 | Criscuolo et al. |
| 2011/0172760 A1 | 7/2011 | Anderson |
| 2011/0178451 A1* | 7/2011 | Robinson .......... A61F 13/00034 602/46 |
| 2011/0213287 A1 | 9/2011 | Lattimore et al. |
| 2011/0224631 A1 | 9/2011 | Simmons |
| 2011/0224632 A1 | 9/2011 | Zimitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Canada |
| 2011/0264138 A1 | 10/2011 | Avelar et al. |
| 2011/0275964 A1 | 11/2011 | Greener |
| 2011/0282136 A1 | 11/2011 | Browning |
| 2011/0282309 A1* | 11/2011 | Adie .................. A61M 1/0088 604/319 |
| 2011/0282310 A1 | 11/2011 | Boehringer et al. |
| 2011/0313374 A1 | 12/2011 | Lockwood et al. |
| 2011/0319804 A1 | 12/2011 | Greener |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Goulthard |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0121556 A1 | 5/2012 | Fraser et al. |
| 2012/0123358 A1 | 5/2012 | Hall et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | De Plessis et al. |
| 2012/0150133 A1 | 6/2012 | Heaton et al. |
| 2012/0157942 A1 | 6/2012 | Weston |
| 2012/0165764 A1 | 6/2012 | Allen et al. |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1 | 8/2012 | Dunn |
| 2012/0220968 A1 | 8/2012 | Confalone et al. |
| 2012/0222687 A1 | 9/2012 | Czajka, Jr. et al. |
| 2012/0277773 A1 | 11/2012 | Sargeant et al. |
| 2012/0302440 A1 | 11/2012 | Theliander et al. |
| 2013/0096518 A1 | 4/2013 | Hall et al. |
| 2013/0110058 A1 | 5/2013 | Adie et al. |
| 2013/0131564 A1 | 5/2013 | Locke et al. |
| 2013/0138054 A1 | 5/2013 | Fleischmann |
| 2013/0150814 A1 | 6/2013 | Buan |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0310781 A1 | 11/2013 | Phillips et al. |
| 2013/0331757 A1 | 12/2013 | Belson |
| 2014/0068914 A1 | 3/2014 | Coward et al. |
| 2014/0088455 A1 | 3/2014 | Christensen et al. |
| 2014/0094730 A1 | 4/2014 | Greener |
| 2014/0163415 A1 | 6/2014 | Zaiken et al. |
| 2014/0180225 A1 | 6/2014 | Dunn |
| 2014/0194836 A1 | 7/2014 | Kazala, Jr. et al. |
| 2014/0194837 A1 | 7/2014 | Robinson et al. |
| 2014/0213994 A1 | 7/2014 | Hardman et al. |
| 2014/0228789 A1 | 8/2014 | Wilkes et al. |
| 2014/0249495 A1 | 9/2014 | Mumby |
| 2015/0005722 A1 | 1/2015 | Hu et al. |
| 2015/0025484 A1 | 1/2015 | Simmons et al. |
| 2015/0065968 A1 | 3/2015 | Sealy et al. |
| 2015/0080947 A1 | 3/2015 | Greener |
| 2015/0112290 A1 | 4/2015 | Dunn |
| 2015/0112311 A1 | 4/2015 | Hammond et al. |
| 2015/0119837 A1 | 4/2015 | Thompson, Jr. et al. |
| 2015/0119865 A1 | 4/2015 | Barta et al. |
| 2015/0148760 A1 | 5/2015 | Dodd et al. |
| 2015/0150729 A1 | 6/2015 | Dagger et al. |
| 2015/0157758 A1 | 6/2015 | Blucher et al. |
| 2015/0159066 A1 | 6/2015 | Hartwell et al. |
| 2015/0174304 A1 | 6/2015 | Askem et al. |
| 2015/0190288 A1 | 7/2015 | Dunn |
| 2015/0196431 A1 | 7/2015 | Dunn |
| 2015/0320602 A1 | 11/2015 | Locke et al. |
| 2016/0030646 A1 | 2/2016 | Hartwell et al. |
| 2016/0166744 A1 | 6/2016 | Hartwell |
| 2016/0354086 A1 | 12/2016 | Dunn |
| 2017/0007462 A1 | 1/2017 | Hartwell et al. |
| 2017/0007751 A1 | 1/2017 | Hartwell et al. |

FOREIGN PATENT DOCUMENTS

| | | |
|---|---|---|
| CN | 101123930 | 2/2008 |
| CN | 101588836 | 11/2009 |
| CN | 102046117 | 5/2011 |
| CN | 102196830 | 9/2011 |
| CN | 102256637 | 11/2011 |
| CN | 102781380 | 11/2012 |
| CN | 203408163 U | 1/2014 |
| DE | 2 949 920 A1 | 3/1981 |
| DE | 10 2005 007016 A1 | 8/2006 |
| EP | 1 320 342 | 6/2003 |
| EP | 2094211 A1 | 9/2009 |
| EP | 2 279 016 | 2/2011 |
| EP | 2 366 721 | 9/2011 |
| EP | 2 368 523 | 9/2011 |
| EP | 2 404 571 | 1/2012 |
| EP | 2 404 626 | 1/2012 |
| EP | 2 341 955 | 12/2012 |
| EP | 2563421 A1 | 3/2013 |
| EP | 2567682 A1 | 3/2013 |
| EP | 2567717 A1 | 3/2013 |
| EP | 2 594 299 | 5/2013 |
| EP | 2 601 984 | 6/2013 |
| EP | 2 623 137 | 8/2013 |
| EP | 2 367 517 | 9/2013 |
| EP | 2 759 265 A2 | 7/2014 |
| EP | 2 829 287 A1 | 1/2015 |
| EP | 2 547 375 B1 | 11/2015 |
| GB | 2389794 | 12/2003 |
| GB | 2423019 | 8/2006 |
| GB | 2489947 | 10/2012 |
| GB | 2496310 B | 5/2013 |
| JP | 2007-505678 | 3/2007 |
| JP | 2007-531567 A | 11/2007 |
| JP | 2008-529618 | 8/2008 |
| JP | 2009-536851 | 10/2009 |
| JP | 2010-526597 A | 8/2010 |
| JP | 2011-500170 A | 1/2011 |

(56) References Cited

FOREIGN PATENT DOCUMENTS

| | | |
|---|---|---|
| JP | 2011-523575 | 8/2011 |
| JP | 2012-513826 A | 6/2012 |
| JP | 2013-526938 A | 6/2013 |
| WO | 1994/20041 A1 | 9/1994 |
| WO | 2001/085248 A1 | 11/2001 |
| WO | WO 2001/89392 | 11/2001 |
| WO | WO 2002/05737 | 1/2002 |
| WO | WO 2003/003948 | 1/2003 |
| WO | WO 2004/018020 | 3/2004 |
| WO | WO 2004/037334 | 5/2004 |
| WO | 2005/046761 A1 | 5/2005 |
| WO | WO 2006/041496 | 4/2006 |
| WO | WO 2006/046060 | 5/2006 |
| WO | 2006087021 A1 | 8/2006 |
| WO | 2007/030601 A2 | 3/2007 |
| WO | 2007/120138 A2 | 10/2007 |
| WO | WO 2007/133618 | 11/2007 |
| WO | 2008/005532 A2 | 1/2008 |
| WO | WO 2008/064502 | 6/2008 |
| WO | 2008/091521 A2 | 7/2008 |
| WO | WO 2008/104609 | 9/2008 |
| WO | WO 2009/019495 | 2/2009 |
| WO | WO 2009/071926 | 6/2009 |
| WO | WO 2009/071933 | 6/2009 |
| WO | WO 2009/112062 | 9/2009 |
| WO | WO 2009/112848 | 9/2009 |
| WO | WO 2009/114624 | 9/2009 |
| WO | WO 2009/156709 | 12/2009 |
| WO | WO 2009/158132 | 12/2009 |
| WO | WO 2010/075180 * | 12/2009 |
| WO | WO 2010/033725 | 3/2010 |
| WO | 2010/051073 A1 | 5/2010 |
| WO | WO 2010/059612 | 5/2010 |
| WO | 2010/079359 A1 | 7/2010 |
| WO | WO 2010/075180 | 7/2010 |
| WO | WO 2010/078349 | 7/2010 |
| WO | WO 2010/092334 | 8/2010 |
| WO | WO 2010/097570 | 9/2010 |
| WO | 2010/147535 A1 | 12/2010 |
| WO | WO 2011/023384 | 3/2011 |
| WO | WO 2011/087871 | 7/2011 |
| WO | WO 2011/091169 | 7/2011 |
| WO | WO 2011/106722 | 9/2011 |
| WO | WO 2011/115908 | 9/2011 |
| WO | 2011/144888 A1 | 11/2011 |
| WO | WO 2011/135286 | 11/2011 |
| WO | WO 2011/135287 | 11/2011 |
| WO | WO 2011/137230 | 11/2011 |
| WO | WO 2012/021553 | 2/2012 |
| WO | WO 2012/038727 | 3/2012 |
| WO | 2012/087376 A1 | 6/2012 |
| WO | WO 2012/082716 | 6/2012 |
| WO | WO 2012/082876 | 6/2012 |
| WO | 2012/106590 A2 | 8/2012 |
| WO | 2012/112204 A1 | 8/2012 |
| WO | 2012/136707 A1 | 10/2012 |
| WO | 2012/142473 A1 | 10/2012 |
| WO | WO 2012/156655 | 11/2012 |
| WO | WO 2012/168678 | 12/2012 |
| WO | 2013/007973 A2 | 1/2013 |
| WO | 2013/012381 A1 | 1/2013 |
| WO | 2013/043258 A1 | 3/2013 |
| WO | 2013/071243 A2 | 5/2013 |
| WO | 2013/074829 A1 | 5/2013 |
| WO | 2013/079947 A1 | 6/2013 |
| WO | 2013/175309 A1 | 11/2013 |
| WO | 2013/175310 A2 | 11/2013 |
| WO | 2014/013348 A2 | 1/2014 |
| WO | 2014/014871 A1 | 1/2014 |
| WO | 2014/014922 A1 | 1/2014 |
| WO | WO 2014/014842 | 1/2014 |
| WO | 2014/024048 A1 | 2/2014 |
| WO | 2014/140578 A1 | 9/2014 |
| WO | 2014/158526 A1 | 10/2014 |
| WO | 2014/165275 A1 | 10/2014 |
| WO | 2015/008054 A1 | 1/2015 |
| WO | 2015/061352 A2 | 4/2015 |
| WO | 2015/109359 A1 | 7/2015 |
| WO | 2015/110409 A1 | 7/2015 |
| WO | 2015/110410 A1 | 7/2015 |
| WO | WO 2016/176513 | 11/2016 |

OTHER PUBLICATIONS

International Preliminary Report on Patentability and Written Opinion, re PCT Application No. PCT/US2012/023754, dated Oct. 2, 2013.
International Search Report and Written Opinion, re PCT Application No. PCT/US2012/023754, dated Jun. 6, 2012.
International Preliminary Report on Patentability and Written Opinion, re PCT Application No. PCT/US2013/050558, dated Jan. 20, 2015.
International Search Report and Written Opinion, re PCT Application No. PCT/US2013/050558, dated Dec. 16, 2013.
Kapischke, et al., "Self-fixating mesh for the Lichtenstein procedure-a prestudy", Langenbecks Arch Surg (2010), 395 pp. 317-322.
International Search Report re PCT/IB2013/002485, dated Apr. 23, 2014.
International Search Report and Written Opinion re PCT/IB2013/001555, dated Sep. 3, 2013.
European Extended Search Report re EP Application No. 12741902.6, dated Aug. 14, 2014.
Non-Final Office Action for U.S. Appl. No. 14/905,266, dated Feb. 1, 2018. 14 pages.
Response with Claims to Non-Final Office Action for U.S. Appl. No. 14/905,266, dated Apr. 25, 2018. 8 pages.
Applicant-Initiated Interview Summary for U.S. Appl. No. 14/905,266, dated Apr. 17, 2018. 3 pages.
English translation of specification, WO 2011/023384 A1 (2011).
The Free Dictionary, Adhere. The Free Dictionary, accessed Mar. 23, 2017, 6 pages. URL: http://www.thefreedictionary.com/adhere.

* cited by examiner

NEGATIVE PRESSURE WOUND CLOSURE DEVICE

CROSS REFERENCE TO RELATED APPLICATION

This application claims the priority to U.S. Application No. 61/439,525, filed Feb. 4, 2011. The entire contents of the above application being incorporated herein by reference.

BACKGROUND OF THE INVENTION

A number of techniques have been developed for treatment of wounds, including wounds resulting from accident and wounds resulting from surgery. Often, wounds are closed using sutures or staples. However, inserting these mechanical closure techniques requires making additional punctures or wounds to the skin, which can result in tissue injury and in the case of excess swelling, possible ischemia and tissue loss. Also, mechanical wound closures such as staples and sutures can cause highly-localized stresses at the insertion points that can impede and damage the normal wound healing processes of the skin.

In recent years, there has been increased interest in using negative pressure devices for the treatment of wounds. Negative pressure wound treatment utilizes devices that remove wound fluids by applying negative pressure suction to the wound. It is believed that such negative pressures promote wound healing by facilitating the formation of granulation tissue at the wound site and assisting the body's normal inflammatory process while simultaneously removing excess fluid, which may contain adverse cytokines bacteria. However, further improvements in negative pressure wound therapy are needed to fully realize the benefits of treatment.

SUMMARY OF THE INVENTION

The present invention relates to a negative pressure wound closure device that specifically exerts force at the edges of the wound to facilitate closure of the wound. The device operates to reduce the need for repetitive replacement of wound filler material currently employed and can advance the rate of healing. The device simultaneously uses negative pressure to remove wound fluids.

In one embodiment, a negative pressure wound closure device includes a wound filler material that is sized and shaped to fit within a wound opening and which contracts along at least one dimension upon application of a negative pressure to the filler material. The filler material is thus configured to preferentially contract in at least one direction and inhibit contractions in one or more additional directions. Prior negative pressure devices did not assist in wound closure, but were used to drain fluids. By providing for the controlled movement of tissue during the healing process in conjunction with the drainage of fluids from wounds as described in connection with the present invention, a substantial improvement in the rate of healing can be realized. Note that depending on the size of the wound, increased negative pressure can be used.

In another preferred embodiment, a tissue grasping surface extends over an outer peripheral surface of the wound filler material and includes a plurality of tissue anchors that engage the tissue at the wound margin. Upon application of negative pressure, the tissue at the wound margin is displaced to facilitate closure of the wound. A negative pressure source, such as a vacuum pump, is coupled to the wound filler material to provide the negative pressure.

The wound filler material generally comprises a porous material, such as a foam. For embodiments employing tissue anchors, these can be integrally formed in the filler material. In other embodiments, the tissue anchors are provided on a separate covering or film that is secured to the filler material.

In preferred embodiments, the filler material includes a stabilizing structure that enables the material to collapse in at least one first direction and inhibits collapse in at least one second direction. The stabilizing structure can include regions of relatively rigid material surrounded by regions of relatively compressible material. In preferred embodiments, the stabilizing structure is an endoskeleton formed of rigid and/or semi-rigid materials.

In certain embodiments, the stabilizing structure inhibits the filler material from collapsing along its height dimension, while enabling the filler material to collapse within the plane defined by the wound margins. This is useful in the case of abdominal surgery, for example, in which the surgical incision is along a straight line to form an oval shaped wound. This generally oval shaped wound can extend through muscle and fatty tissue having variable mechanical properties. Wound healing is better served through the use of an oval shaped structure adapted to preferentially collapse towards the original line of incision. In preferred embodiments, the stabilizing structure promotes collapse of the filler material in a manner to effect reapproximation of the wound tissue. Fasciotomy wounds, or other wound dehiscences, or any open wound can be successfully treated using embodiments of the present invention.

The wound closure device can be used to treat wounds in the mediastinum, for pressure ulcers, for wounds in the extremities (arms or legs) etc. The wound closure device can also be used to treat wounds of different shapes, such as circular, square, rectangular or irregularly shaped wounds. A plurality of wound closure elements can be shaped to fit within a wound and can attach together to preferentially close the wound in a desired direction. The different elements can comprise different materials or have different characteristics, such as pore size and/or anchor size and distribution to form a composite structure.

In one embodiment, an endoskeleton stabilizing structure includes a plurality of spaced-apart rigid members forming a cross-hatched configuration. The endoskeleton enables the filler material to collapse along its width dimension and elongate to a smaller degree along its length dimension. In certain embodiments, a plurality of rigid members extend along the height of the filler material and inhibit collapse of the material in its height dimension, for example. According to certain embodiments, the endoskeleton comprises a network of interconnected rigid members that can articulate with respect to one another during collapse of the filler material. The endoskeleton can include truss supports to inhibit tilting motion of the filler material. In some embodiments, the tissue anchors can be integrally formed in the endoskeleton.

In certain embodiments, the wound filler material includes a smooth bottom surface having micropores to allow the passage of fluid from the wound through the bottom surface and into the device for removal. The micropores can have variable pore size and/or pore density to direct the distribution of vacuum force from the negative pressure source. In some embodiments, the wound filler material can have variable internal pore sizes and/or pore density to direct the distribution of vacuum force.

In one embodiment, a negative pressure wound treatment component for managing and/or removing fluid is coupled to the wound filler material. A single negative pressure source can be used for wound closure and fluid management/drainage. A sliding surface is provided at the interface between the wound closure and fluid management components.

In yet another embodiment, the filler material includes removable portions to adjust the size of the wound closure device. The filler material can be provided with pre-determined cleavage lines for tearing or cutting away portions of the material. In certain embodiments, sets of tissue anchors are embedded in the filler material, and become exposed by removing excess portions of the material.

According to another embodiment, the tissue anchors are provided with a variable force profile. The force profile can vary based on the depth of tissue or the type of tissue engaged. In some embodiments, the force profile of the tissue grasping surface varies around the perimeter of the wound closure device. The force profile is varied, for instance, by varying one or more of the length of the tissue anchors, the shape of the anchors, the materials of the anchors and the density of the anchors.

The present invention also relates to methods of closing a wound using a wound closure device as described above. For example, a linear incision in the skin overlying the abdomen provides access to a surgical site such as the gastrointestinal system of the human or animal body. Following completion, the wound must be treated by negative pressure therapy to facilitate recovery. Thus, a wound closure device in accordance with preferred embodiments of the invention is inserted for wound closure treatment.

By using the negative pressure wound closure device of the invention, patients with large or severe wounds are able to be discharged or engage in rehabilitative physical therapy, changed at home and then brought back to have their wounds simply stitched closed. By improving wound closure treatment and thereby reducing cost, there is an opportunity for these devices to be a significant part of the instruments used for wound care.

BRIEF DESCRIPTION OF THE DRAWINGS

Other features and advantages of the present invention will be apparent from the following detailed description of the invention, taken in conjunction with the accompanying drawings of which.

DETAILED DESCRIPTION OF THE INVENTION

Figure 1A:
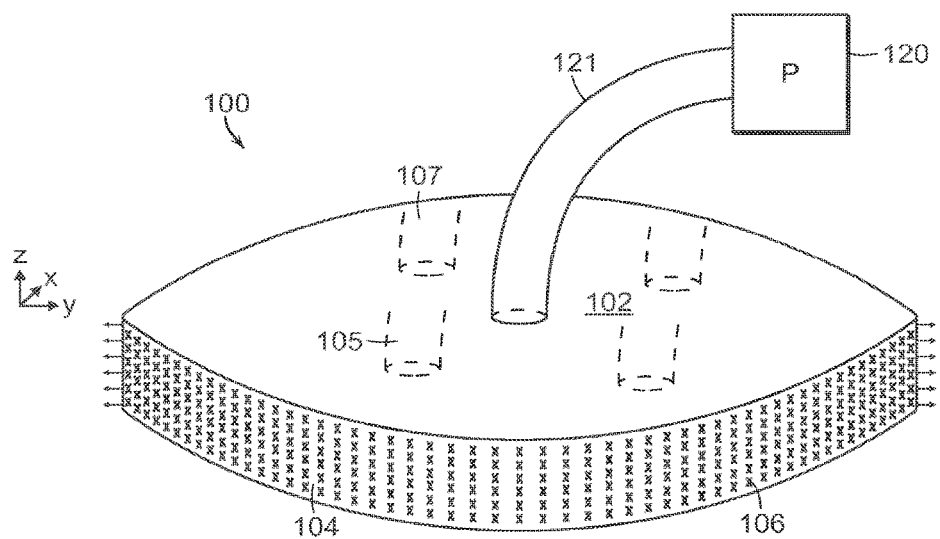
FIG. 1A is a perspective schematic view of a negative pressure wound closure device.

FIGS. 1A-1F illustrate an embodiment of a wound closure device 100 of the present invention. The device 100 includes a wound filler material 102 that is sized and shaped to fit within a wound opening of a human or animal patient. In preferred embodiments, the filler material 102 is a porous, biocompatible material, such as an open cell polyurethane foam. The filler material 102 is also preferentially collapsible, meaning that its size can be reduced along at least one dimension (e.g., length, width, height) by applying a negative pressure to the filler material 102, while at the same time inhibiting contractions or contracting at a slower rate in another direction.

Extending over at least one surface of the filler material 102, and preferably extending over an outer perimeter surface of the filler material 102 is a tissue grasping surface 104. In one embodiment, the tissue grasping surface 104 is a flexible covering, such as a mesh film, that is secured to the outer perimeter surface of the filler material 102 and can expand and contract with the expansion and contraction of the filler material 102. In one embodiment, the tissue grasping surface 102 is a mesh film or a composite polyester mesh film, such as the Parietex™ mesh from Covidien (Mansfield, Mass.). The tissue grasping surface 104 includes a plurality of outward-facing tissue anchor elements 106, which in the preferred embodiment are a plurality of closely-spaced barbs, hooks or tissue grasping elements, which can be integrally formed in the mesh film.

Figures 1B, 1C:
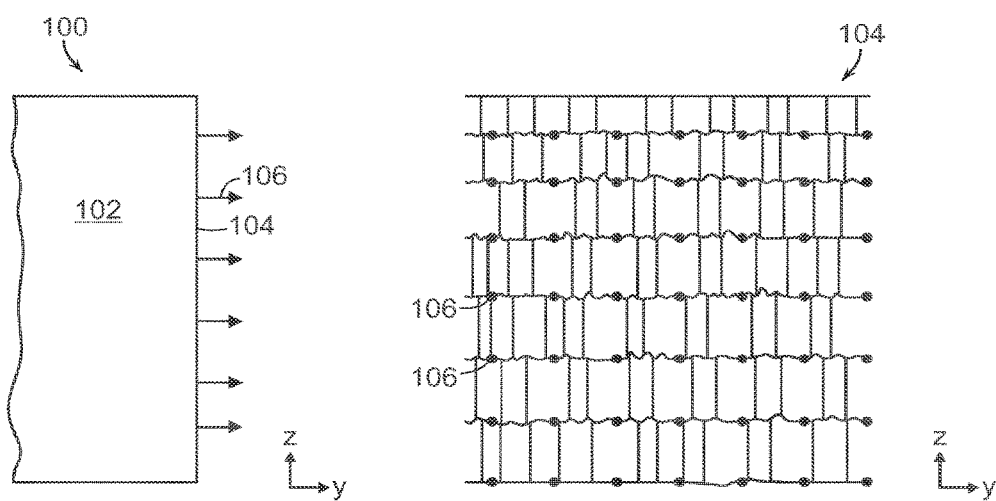
FIG. 1B is a cross-section view of the tissue grasping surface of the wound closure device.
FIG. 1C is a side view of one embodiment of the tissue grasping surface.

FIG. 1B is an edge view of the device 100 showing the tissue grasping elements 106 projecting from the tissue grasping surface 104 on the periphery of the wound filler material 102. FIG. 1C is a side view of one embodiment, in which the tissue grasping surface 104 is formed from a flexible material, in particular, a mesh material. The grasping elements 106 project out from the page in FIG. 1C. The flexible, mesh material of the tissue grasping surface 104 allows the surface to expand and contract as necessary with the expansion and contraction of the underlying wound filler material 102.

In other embodiments, the tissue grasping surface 104 with anchor elements 106 can be integrally formed in the filler material 102. The tissue grasping surface and/or anchor elements can also be formed using a resorbable material.

The tissue anchor elements 106 are preferably provided over an entire outer perimeter surface of the filler material 102. When the filler material 102 is placed within a wound, the anchor elements 106 become buried within the tissue at the wound margins and secure the device 100 within the wound opening. The tissue anchor elements 106 are preferably spread out over the entire surface of the wound margin to provide sufficient strength in the grasping force. The tissue grasping surface 104 is preferably designed to allow the wound closure device 100 to be easily placed but also easily removed and replaced with a new device 100 or other wound dressing as needed (e.g., 2-7 days later). The grasping surface 104 can be configured to have high grasping strength over at least a portion of its surface, but easily removable by, for example, pulling away at an edge. The tissue grasping surface 104 is preferably designed to be removed from a wound without damaging the surrounding tissue. The anchor elements 106 are preferably designed to accommodate various tissue applications, such as muscle, fat, skin and collagen, and various combinations of these. The anchor elements 106 can also be designed to remain securely attached to particular tissues for a selected time period in certain embodiments.

In embodiments in which the grasping surface 104 is formed from a covering on the outer peripheral surface of the filler material 102, the grasping surface can be attached to the filler material 102 using any suitable technique, such as with an adhesive or a mechanical fastening system. In a preferred embodiment, the tissue grasping surface 104 includes filler grasping anchor elements, which can be barbs, that secure the grasping surface to the filler material. As shown in the cross section view of FIG. 6, for example, the grasping surface 400 comprises a thin mesh or film having two sets of barbs or similar anchor elements, a first set 410 of outwardly-facing tissue-grasping elements 412 that are designed to project into tissue, and a second set 404 of elements 406 that project into the filler material to secure the grasping surface to the filler material.

Returning to FIGS. 1A-1F, a negative pressure source 120, such as a pump, is coupled to the filler material 102 by a suitable coupling or conduit, such as tube 121. Additional tubes 107 can also be connected through an array of spaced ports 105 in order to spatially distribute the suction force so that the force exerted along the sidewall 104 can be controlled separately from a fluid suction force. The negative pressure source 120 can be activated to apply a negative pressure to the filler material 102. In general, the negative pressure causes a resulting pressure differential which causes the filler material 102 to contract or "collapse." As the filler material 102 contracts, the tissue grasping surface 104 grabs and pulls on the adjacent tissue, which is preferably the tissue around a wound margin, resulting in the displacement of the tissue thereby facilitating the closure of the wound. In a preferred embodiment, the filler material 102 is designed to collapse preferentially in at least one direction. For example, in the embodiment of FIG. 1A, the filler material 102 includes a length and width dimension along the y- and x-axes, respectively, and a height along the z-axis. In order to efficiently transmit the negative pressure to the subcutaneous or other wound margins, it is preferred that the filler material 102 does not collapse centrally in the z-direction (like a pancake), so that the action of the negative pressure works predominantly in the x-y directions, or more particularly, in a two dimensional plane along the wound margins such as in an open abdomen or fasciotomy. It will be understood that in some embodiments, the plane of the wound margins can be curved, such as when the wound goes around the curve of an abdomen or leg.

Furthermore, in preferred embodiments the filler material 102 is configured to preferentially collapse in length and/or width (i.e., along the x- and y-axes) to reapproximate the tissue at the wound margins. Note that certain types of wounds can be treated without the anchor elements described herein.

There are several ways in which the filler material 102 is configured to exhibit preferential collapse characteristics. For example, portions of the filler material 102 can be made from more rigid material than the surrounding material, causing the filler material to preferentially collapse in a particular direction. In one embodiment, the filler material 102 can include a stabilizing endoskeleton made from a suitable rigid material embedded within a "collapsible" filler, such as an open cell foam. Note that the amount of applied negative pressure can be adjustable depending on the size and shape of the wound. Pressures above 125 mm, to as much as 250 mm or more can be used to assist in wound closure. The pressure can be reduced over time as the wound contracts.

Figure 1D:
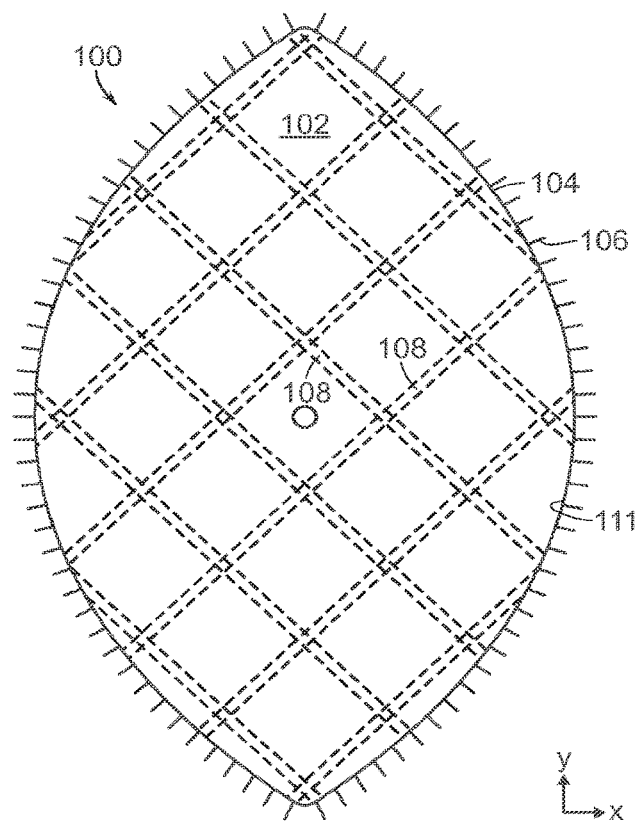
FIG. 1D is a top view of the wound closure device showing x-y stabilizers in phantom.
Figure 1E:
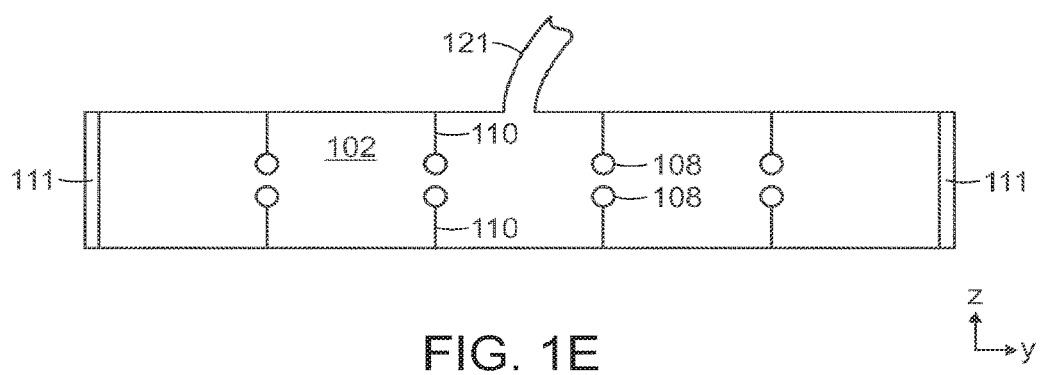
FIG. 1E is a cross-section view of filler material showing x-y stabilizers and z-stabilizers.

As shown in FIGS. 1D and 1E, for example, the filler material 102 includes a plurality of stabilizer elements 108 (shown in phantom) that enable the collapse of the filler material in certain directions, while inhibiting it in other directions. In this embodiment, the stabilizer elements 108 include a plurality of stabilizing ribs, flexures or rods, made from a suitably rigid or semi-rigid material, such as plastic. The ribbed structure is configured to preferentially collapse along a specific axis to facilitate proper closure of the wound. The internal stabilizer elements 108 in this embodiment form a cross-hatched pattern as seen in FIG. 1D, though it will be understood that other configurations can be utilized. The spacing between the elements in the "open" state can be in a range of 1-2 cm, for example. The stabilizer elements 108 can be provided at different depths within the filler material, as shown in the cross-section view of FIG. 1E, which helps inhibit collapse in the z-direction. In some embodiments, z-axis stabilizer elements 110 can be utilized to inhibit collapse in this direction. In FIG. 1E, the z-axis stabilizer elements 110 are projections that extend vertically from the ribs 108. In other embodiments, separate z-axis stabilizers, such as rods or rib structures, can be employed.

In certain embodiments, the device 100 can include a peripheral stabilizer element 111 that extends around the outer periphery of the filler material 102, as shown in FIG. 1E. The stabilizer element 111 can include a rib structure that reinforces the filler material 102 in order to prevent collapse in the z-direction, as well as to inhibit tilting of the filler material in the z-y and z-x planes. Thus, preferred embodiments of the filler material preferentially contract in at least a first direction relative to a second direction upon application of a negative pressure. Thus, for example, the width will contract at a faster rate relative to the length, while the height (depth of the wound) does not contract a substantial distance.

In some embodiments, the tissue grasping anchor elements 106 can be included on the peripheral stabilizer element 111, and project out from the periphery of the filler material 102. This can be as an alterative to, or in addition to, providing the anchor elements 106 on a separate mesh or film. The peripheral stabilizer element 111 is preferably configured to expand and contract as necessary with the expansion and contraction of the wound filler material 102. Thus, in a preferred embodiment, the stabilizer element 111 has sufficient flexibility to contract and expand in the x- and y-directions (i.e., around the periphery of the filler material 102), but has adequate rigidity along the z-direction (i.e. along the height of the filler) to inhibit collapse or tilting in this direction.

Figure 1F:
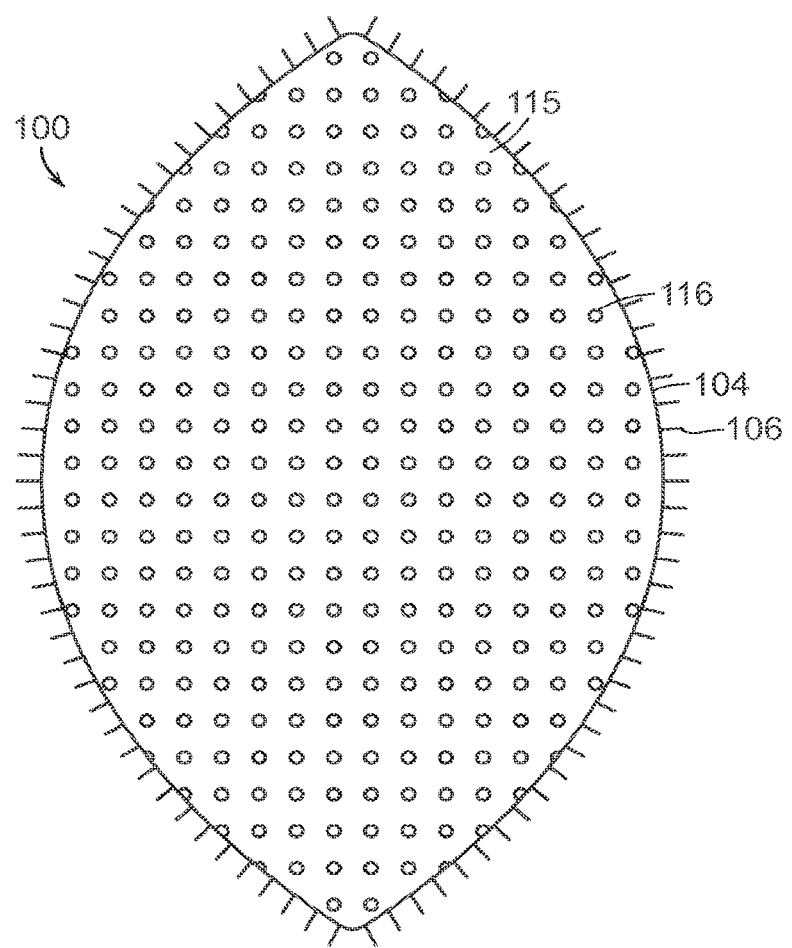
FIG. 1F is a bottom view of the wound closure device showing a smooth bottom surface and micropores for removing fluid from the wound site.
Figure 1G:
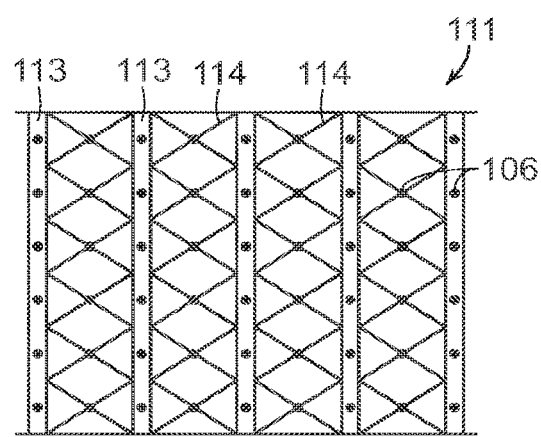
FIG. 1G is an elevation view of a peripheral stabilizer element.

An embodiment of a peripheral stabilizer element 111 is shown in elevation view in FIG. 1G. The stabilizer element 111 includes a plurality of stabilizing rods 113, oriented to inhibit collapse in the z-direction. The rods 113 are separated by a flexible material 114 that allows the stabilizer element 111 to expand and contract around the wound margin with the expansion and contraction of the underlying filler material. In this embodiment, the tissue anchor elements 106 are formed in the peripheral stabilizer element 111 and project out from the page.

Figure 2A:
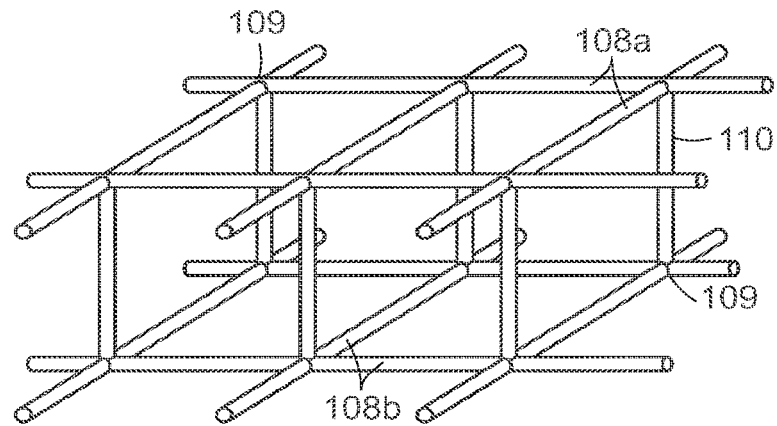
FIGS. 2A and 2B are perspective and side views, respectively, of a supporting endoskeleton.
Figure 2B:
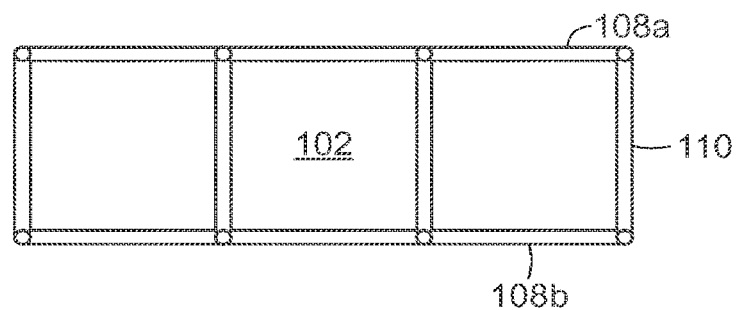

One embodiment of an endoskeleton for a wound filler material of the invention is shown in FIGS. 2A and 2B. The endoskeleton includes a first set of x-y stabilizer elements 108a and a second set of x-y stabilizer elements 108b that are connected by a plurality of z-axis stabilizer elements 110. During collapse of the filler material 102, the respective x-y stabilizer elements 108a, 108b are collapsible in the x-y directions, but the z-axis stabilizer elements 110 inhibit collapse in the z-direction. In preferred embodiments, the stabilizer elements can articulate with respect to one another during collapse. The joints 109 in the structure can be hinged or have a reduced thickness to accommodate the flexing of the system. The flexures between the joints may also flex to accommodate the desired compression along the first, or lateral, axis 117 (see FIG. 4B). Some expansion can occur along the second, or longitudinal, axis 119 as the device compresses. The frame material can have a shape memory characteristic, which in combination with the suction force, 25 defines the force level applied to the tissue.

Figure 3A:
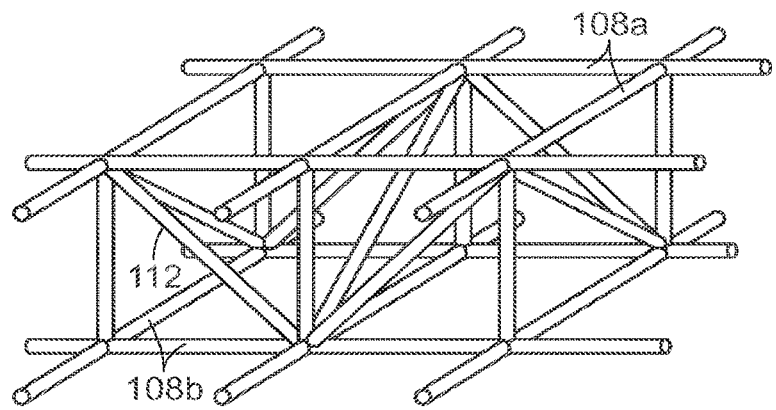
FIGS. 3A and 3B are perspective and side views, respectively, of a supporting endoskeleton with support trusses.
Figure 3B:
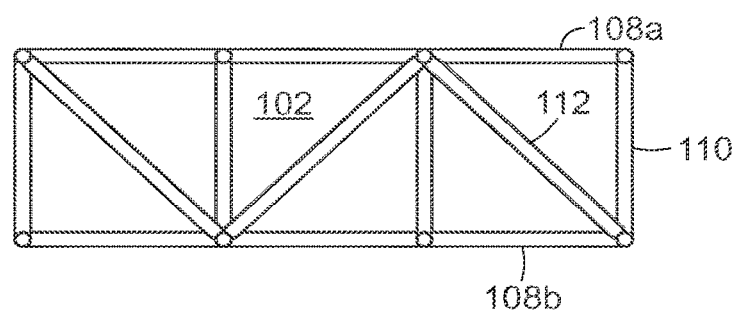
Figure 3C:
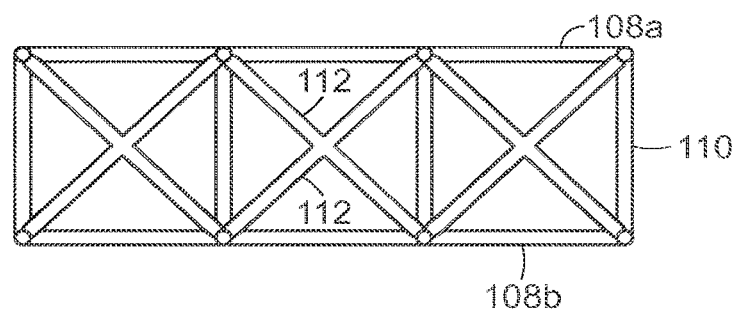
FIG. 3C is a side view of a supporting endoskeleton with x-shaped support trusses.

In another embodiment, shown in FIGS. 3A and 3B, the endoskeleton includes truss stabilizers 112 to inhibit tilting of the filler material 102 during collapse. The truss stabilizers 112 keep the upper 108a and lower 108b x-y stabilizers aligned with one another as the filler material 102 collapses. In some embodiments, the truss stabilizers 112 can be rigid in certain directions and relatively less rigid in other directions (for example, the truss stabilizer can be bowed) to promote collapse in certain directions. FIG. 3C illustrates an alternative embodiment having truss stabilizers 112 in an "x"-shaped pattern.

The stabilizing endoskeleton in certain embodiments can be made, in whole or in part, from a shape memory material. Various shape memory materials can be used which return from a deformed state (temporary shape) to their original (permanent) shape. This change in shape can be induced by an external stimulus or trigger. In one embodiment, the original or "permanent" shape of the endoskeleton is the "collapsed" configuration of the wound closure device, or the shape that will bring about wound reapproximation. When the wound closure device is initially inserted in the wound opening, the endoskeleton is in a deformed or temporary state and embedded within the filler material. The endoskeleton can preferentially revert to its original or "collapsed" state or, alternatively, cause the device to expand to engage the tissue. The "collapse" force of the shape memory endoskeleton can be in addition to or an alternative to the vacuum force induced by the negative pressure source. In certain embodiments, the application of a negative pressure to the wound closure device, which can cause the endoskeleton to revert to its original state.

FIG. 1F shows the bottom of the wound closure device 100 according to one embodiment. The device 100 in this embodiment includes a smooth bottom surface 115. This material can be biocompatible film to be used with, such as, provided in conjunction with the Renasys® system available from Smith & Nephew. A preferred embodiment can also be used with a gauge as also provided in the Renasys® system. The bottom surface 115 provides a low friction interface between the wound closure device 100 and the underlying tissue. In the case of an abdominal wound, for example, the underlying tissue can include internal organs, such as the intestines. The smooth bottom surface 115 enables the filler material 102 to contract and expand freely without interference from the underlying tissue, and without damaging the underlying tissue. In a preferred embodiment, the bottom surface 115 includes micropores 116 (shown with size exaggerated in FIG. 1F for purposes of illustration) that allow the passage of fluid through the bottom surface 115 and into the device 100 for removal from the wound site. The wound closure device can also be inserted over a separate layer of material so that the device with contract on top of the sliding layer.

In some embodiments, the micropores 116 can have different sizes in different regions and/or can have different pore densities in different regions in order to direct different force levels of the vacuum source to different regions of the device 100. Similarly, the filler material 102 can be engineered with different internal pore sizes and/or pore densities to direct the distribution of forces from the vacuum source to different areas of the device 100.

Figure 4A:
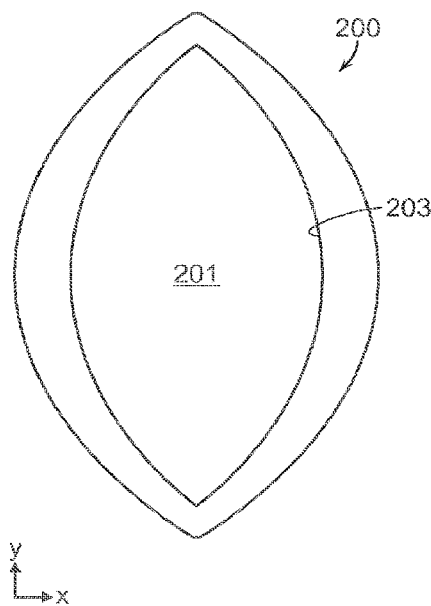
FIGS. 4A-C illustrate a wound closure device of the invention closing a wound.
Figure 4B:
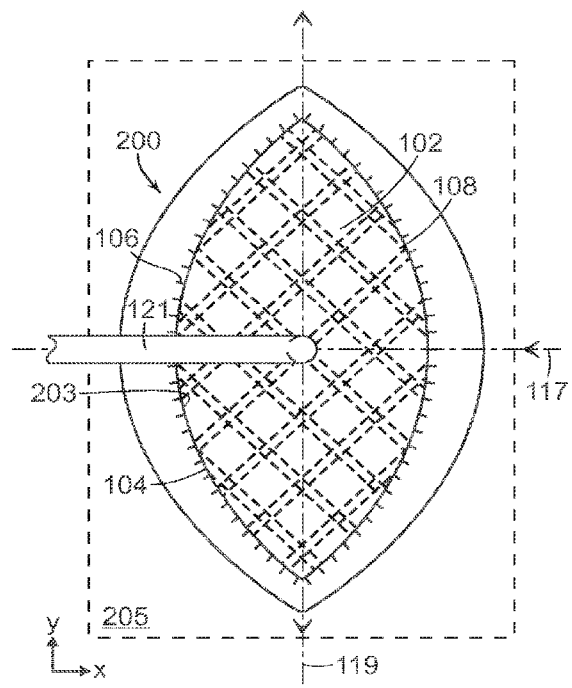
Figure 4C:
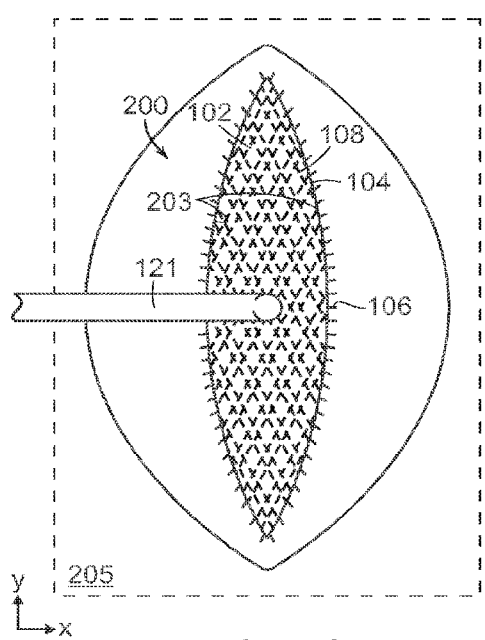

FIGS. 4A-4C illustrate the use of the present device 100 to close a wound 200. The wound 200 includes a wound opening 201 and a wound margin 203, as shown in FIG. 4A. In FIG. 4B, a wound closure device 100 is placed within the wound opening 201 so that the tissue grasping surface 104 is contacting the wound margin 203. In certain embodiments, the wound closure device 100 can be formed by trimming or tearing the filler material 102 to the proper size, and then attaching the tissue grasping elements 106 around the periphery of the filler material 102. In one embodiment, the grasping elements 106 are attached by attaching a two-sided barbed mesh to the filler material 102, where the outward facing prongs are designed for grasping tissue and the inward facing prongs are designed to secure the mesh to the filler material 102. A tube 121 connects the filler material 102 to the negative pressure source. The area of the wound 200, including the filler material 102, can be covered by a sealing drape 205.

In the embodiment of FIG. 4B, the filler material 102 includes a plurality of internal stabilizer elements 108 (shown in phantom) that provide the filler material 102 with a preferential collapse characteristic. The stabilizer elements 108 help control the collapse of the filler material 102, and the resulting displacement of the tissue around the wound margin 203, in the x- and y-directions. Additional stabilizer elements can be provided to control or inhibit collapse along the z-direction. As described above in connection with FIG. 1D, the stabilizer elements 108 in this embodiment include a crosshatched configuration.

Figure 4D:
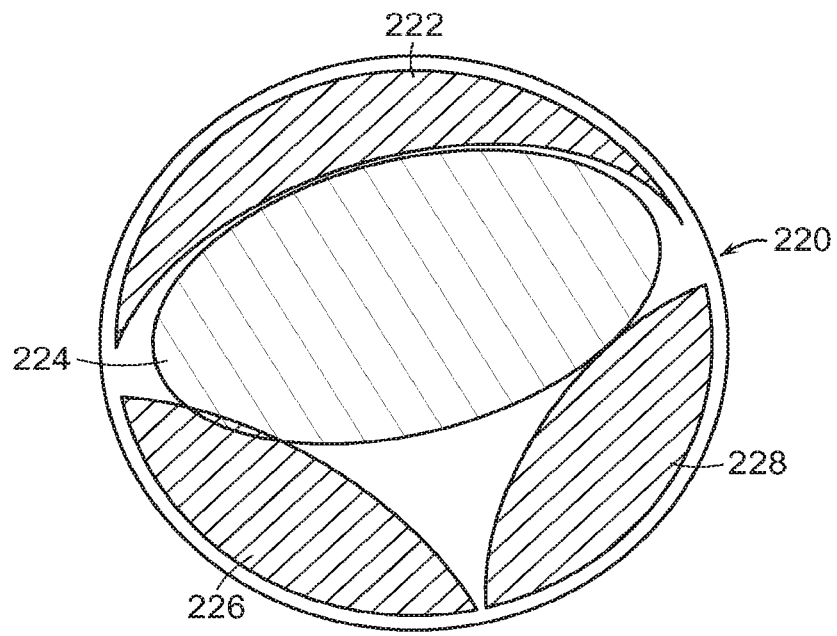
FIGS. 4D-4E illustrate the use of a plurality of wound closure elements used for wounds of different shapes.
Figure 4E:
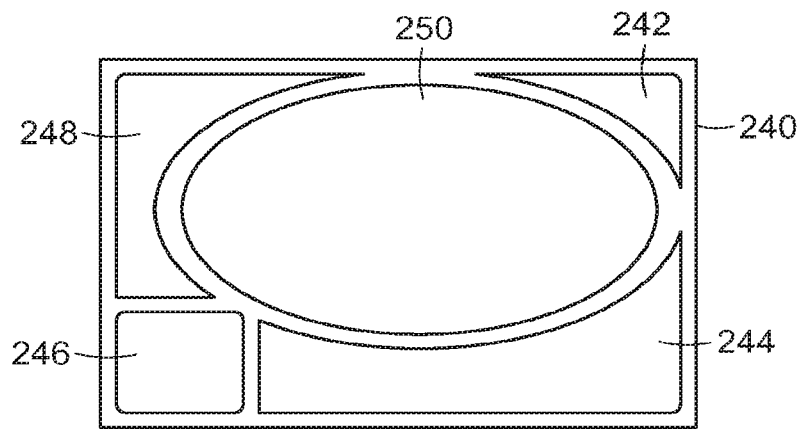

FIG. 4C illustrates the wound 200 following the application of a negative pressure to the wound closure device 100. The tissue anchor elements 106 grab the tissue margins 203 and cause displacement of the tissue margins 203 as the filler material 102 collapses. As seen in the FIG. 4C, the filler material 102 collapses in the x- and y-directions in such a manner as to reapproximate the tissue at the wound margin 203. In the embodiment of FIGS. 4B and 4C, the crosshatched configuration of the stabilizer elements 108 help control the direction of tissue displacement during collapse. The largest amount of tissue displacement in this embodiment is in the central region of the wound 200, where the opening 201 is widest, and this displacement is primarily inward along the x-direction. Away from the central region (e.g., at the top and bottom of the wound as shown in FIGS. 4A and 4B), where the wound margins are closer together, less displacement in the x-direction is needed to reapproximate the tissue. In general, the inward collapse of the filler material along the y-direction is undesirable. In fact, during tissue reapproximation, the wound 200 will tend to elongate in y-direction as the wound margins close in the x-direction. In preferred embodiments, the internal stabilizer elements 108 promote the collapse of the filler material in a manner that provides wound reapproximation. In the embodiment of FIGS. 4-C, for example, during filler collapse the crosshatched stabilizer elements 108 straighten out relative to one another, similar to an accordion gate. The largest displacement is in the central region of the filler 102, along the x-direction. The stabilizers 102 generally inhibit inward collapse along the y-direction. As the stabilizers 108 straighten out, they can also facilitate elongation of the wound in the y-direction to allow proper tissue reapproximation. Shown in FIGS. 4D-4E are different shaped wounds 220, 240 in which a plurality of wound closure elements are used in combination to fill the wound. In FIG. 4D, elements 222, 224, 226 and 228 have different shapes that are cut or trimmed to size so as to substantially fill the wound that in this example, is circular in shape. When negative pressure is applied, the elements work together to close the wound in a desired direction. FIG. 4E illustrates a rectangular wound 240 using closure elements 242, 244, 246, 248 and 250 to fill the wound 240. The tissue anchors of each closure element can also attach to the adjoining closure element(s). With suction applied to the central elements 224, 250, the adjoining elements are drawn towards the central elements to close the wound.

The wound closure device 200 can remain in this configuration for a period of several days or weeks to facilitate closing and healing of the wound 200. After a period of healing, the device 100 can be removed and optionally replaced with a smaller device. After the wound has been sufficiently closed using the present device, it can be stitched closed.

Figure 5:
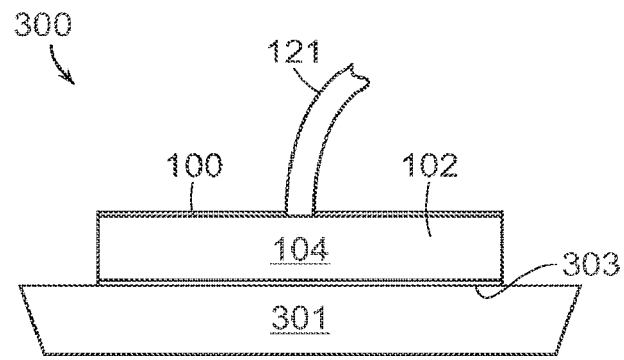
FIG. 5 illustrates a two stage negative pressure wound treatment and negative pressure wound closure (NPWT/NPWC) device.

FIG. 5 illustrates a two stage negative pressure wound treatment and negative pressure wound closure (NPWT/NPWC) device 300. The device includes a negative pressure drainage/fluid management component 301, as is known in the art, that connects with an overlying negative pressure wound closure device 100. The wound closure device 100 includes a collapsible wound filler material 102 and a tissue grasping surface 104, substantially as described above. A tube 121 connects the device 300 to a single pump for applying a negative pressure to the wound closure and wound treatment components. The device 300 can include interchangeable parts depending on the need of a specific wound application. In one embodiment, the device 300 is used for abdominal wounds, and can also be used for mediastinum and fasciotomy wounds.

In a preferred embodiment, the filler material 102 is able to "slide" within the total NPWT/NPWC device 300. The filler material 102 includes a sliding surface 303 at the interface between the wound closure and fluid management components. The sliding surface can comprise a treated surface or a separate layer of material. The sliding surface 303 facilitates the free contraction of the wound closure component, without interference from the fluid management component. The underlying fluid management component 301 can be specifically configured to manage fluid only and to not generate granulation, as this can slow down or inhibit the "slide."

Figure 6:
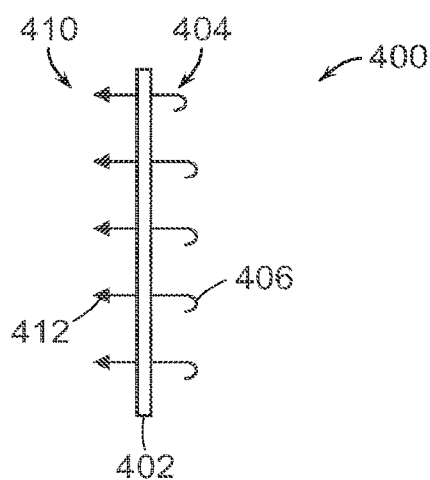
FIG. 6 illustrates an enlarged view of a preferred embodiment of the tissue anchor system in accordance with the invention.

FIG. 6 illustrates an enlarged view of a preferred embodiment of the tissue anchor system 400 in accordance with the invention. One side of the material 402 has a first group of anchor elements 404 that are adapted to grasp the filler material. The first anchor elements 404 can be shaped to grasp the filter material such as with a distal hooked shape 406. As material 402 must attach to the filter with a certain grasping strength in order to apply a sufficient pulling force on the tissue, a specified force level F, must be applied to remove the hooks from the filler material that exceeds the pulling force being applied to the tissue. Similarly, as the tissue to be grasped by the material 402 has different structural characteristics then the filler material, a second group of anchor elements 410 adapted to grasp tissue can have a different shape and grasping force then the first anchor elements. In this embodiment, barbs 412 will bilateral prongs 414 that tend to collapse upon insertion in tissue and yet expand when pulled in an opposite direction such that a certain pulling force can be applied to tissue. However, the prongs or cone shape anchor element has a release force such that the barbs can be manually pulled from the tissue without causing injury.

Figure 7:
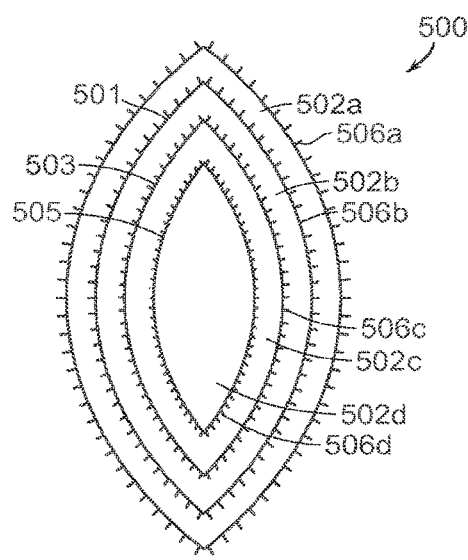
FIG. 7 illustrates an embodiment of a wound filler material having a tear-away or cut-away design for accommodating different wound sizes, with tissue anchors embedded within the filler material at pre-determined cleavage points.

FIG. 7 illustrates an embodiment a wound filler material 500 having a tear-away or cut-away design for accommodating different wound sizes. The filler material 500 includes natural cleavage lines 501, 503, 505 that allow the size of the material to be adjusted to fit the wound to be closed. The material 500 is designed to be torn or cut at the cleavage lines to remove one or more portions 502a, 502b, 502c of the material and adjust the size of the material. Sets of tissue anchors 506a, 506b, 506c, 506d are embedded within the filler material at pre-determined cleavage points, and become exposed as the respective outer portions 502a, 502b, 502c are removed. The tissue anchors 506a, 506b, 506c, 506d can be associated with a stabilizing endoskeleton structure, such as described above in connection with FIGS. 1-4. In some embodiments, the stabilizing endoskeleton structure can include pre-defined cleavage points to remove portions of the stabilizer structure as the size of the filler material 500 is adjusted.

Figures 8A, 8B:
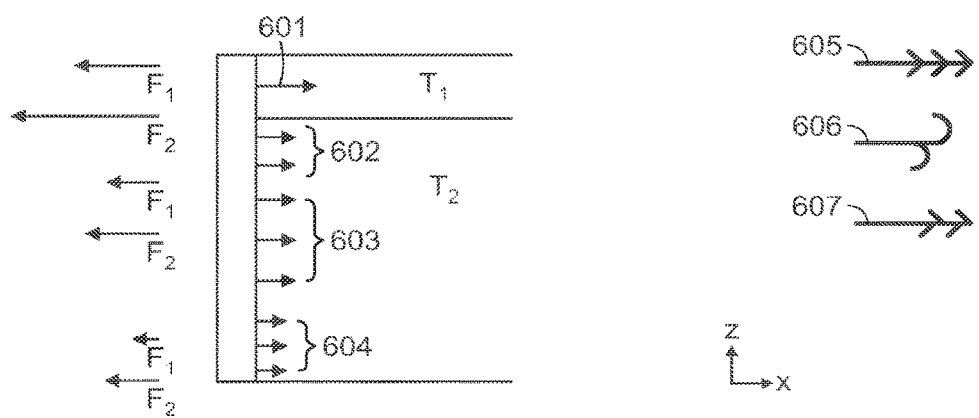
FIG. 8A is a side view of a tissue grasping surface, illustrating different tissue anchors for different types of tissue ($T_1$, $T_2$) and the respective force profiles for the anchors, including the maximum force applied during vacuum closure ($F_1$) and the force required to remove the anchors from the tissue ($F_2$) without damaging the tissue.
FIG. 8B illustrates different designs for a tissue anchor of the invention.

FIG. 8A is a side view of a tissue grasping surface, illustrating different tissue anchors 601, 602, 603, 604 for different types of tissue ($T_1$, $T_2$). Also illustrated is an example of the respective force profiles for the anchors, including the maximum force applied to the tissue during vacuum closure ($F_1$) and the force required to remove the anchors from the tissue ($F_2$) without damaging the tissue. In one embodiment, the characteristics of the tissue anchors vary to provide different force profiles across the interface between the wound closure device and the surrounding tissue. For example, for the upper tissue layer(s), $T_1$, the anchor 601 is designed to attach to collagen material, such as in the dermis. The anchor 601 has a different force profile ($F_1$ and $F_2$) on the upper tissue layer(s), $T_1$, as shown in FIG. 8A. At the lower tissue layers $T_2$, the anchors 602, 603, 604 are designed to attach to fatty tissue of subcutaneous layer. Generally, a smaller force profile is needed to secure the anchors to this tissue.

Figure 8C:
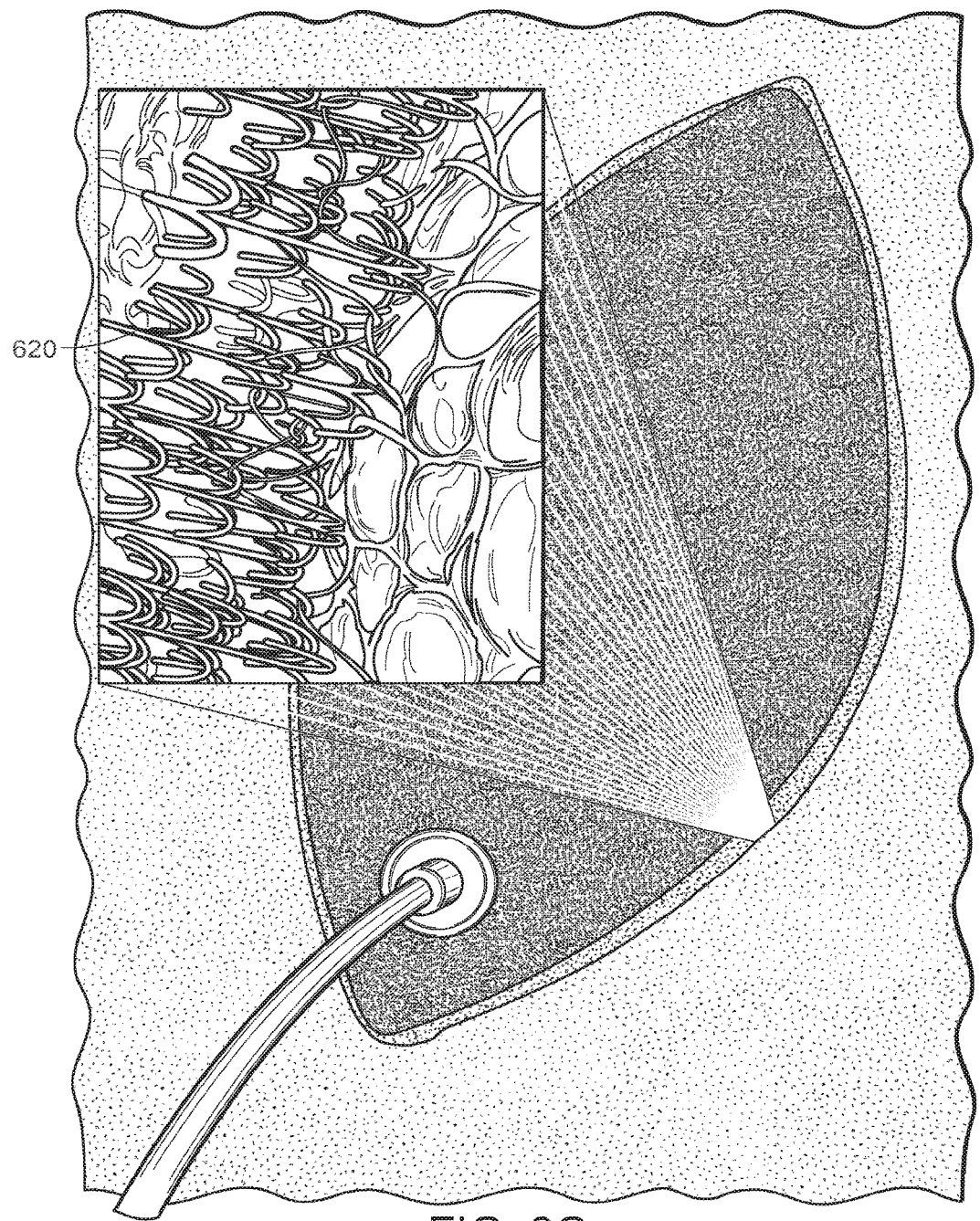
FIG. 8C illustrates an enlarged view of tissue anchor elements on the peripheral surface of an oval shaped wound closure device.

The characteristics of the anchors, and their resulting force profiles, can vary by a number of parameters, such as the length of the anchor, the shape of the anchor, the structure of grasping features, the material(s) used for the anchor, the relative flexibility/rigidity of the anchors, and the spacing/density of the anchors. In FIG. 8A for example, anchor 601 is significantly longer than anchors 602, 603, which in turn are longer than anchors 604. FIG. 8A also illustrates varying the density of anchors, such as shown in 602, 603 and 604. FIG. 8B illustrates three examples of different types of grasping features, including a barbed configuration 605, a staggered hook configuration 606, and a staggered barbed configuration 607. Other suitable grasping features can be utilized such as the anchor elements 620 shown in the enlarged perspective view of FIG. 8C. The anchoring process can be augmented by suturing the filler material or supporting endoskeleton to the tissue. The force profile can also be varied by controlling the vacuum force distribution in the filler material, such as by varying the pore size and/or pore density of the filler.

The wound closure device of the invention can be provided in kits for closing different types of wounds (e.g., abdominal, fasciotomy, etc.). The tissue grasping surface can be optimized for different types of tissue such as collagen, fatty tissue and muscle, depending on the structure of the tissue at the wound site.

Figure 9A:
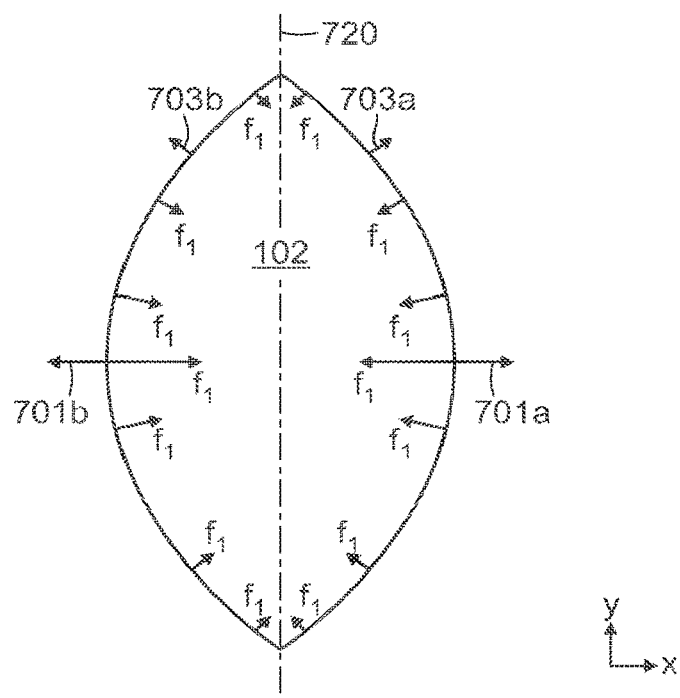
FIG. 9A is a schematic illustration of a wound closure device positioned within a wound showing the different force profile around the margin of the wound according to one embodiment.
Figure 9B:
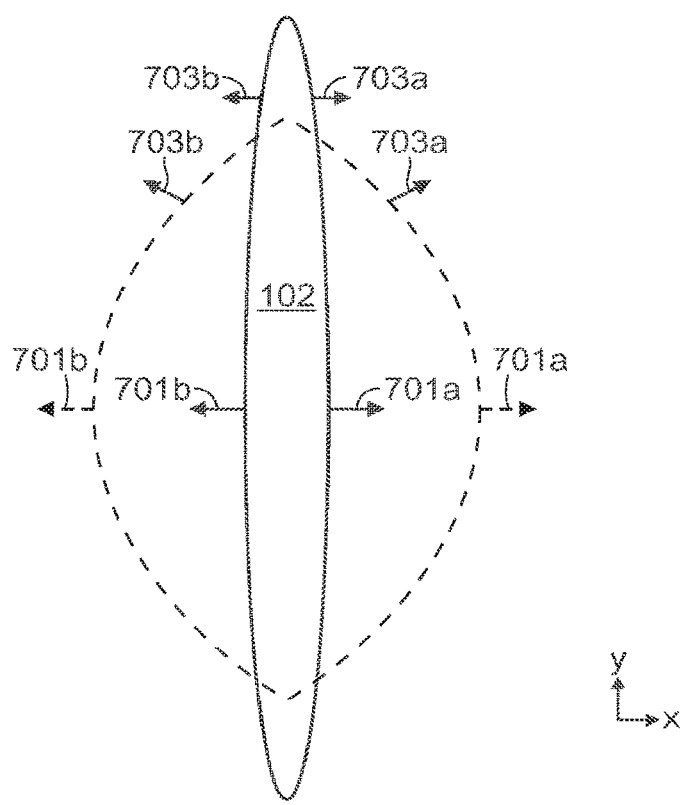
FIG. 9B illustrates the wound closure device of FIG. 9A after a period of wound closure and healing, with the original configuration of the wound and wound closure device indicated in phantom.

In certain embodiments, the force profile of the wound closure device is variable around the periphery of the wound. An exemplary embodiment is illustrated in FIG. 9A, which shows the force profile ($f_1$) exerted on the wound margins at a plurality of locations on the periphery of the wound. In this embodiment, the largest $f_1$ is at the central region of the wound filler 102, where the wound opening is widest and the wound closure force is entirely or nearly entirely in the x-direction. Moving towards the top and bottom regions of the wound, the closure force ($f_1$) is much smaller. One reason for this is because the wound opening is much smaller in these regions, and a much smaller force is needed to reapproximate the tissue. Also, the inward force exerted in these regions includes components in both the x- and y-directions. Thus, a smaller force profile is preferable to avoid the inward collapse of the tissue in the y-direction. As illustrated in FIG. 9B, as the wound closes and heals from an initial state (indicated by dotted lines) to a later state (indicated by solid lines), it becomes elongated in the y-direction. Thus, the displacement of tissue anchors 701*a* and 701*b* is exclusively in the x-direction and in the direction of the closure force ($f_1$), while the displacement of tissue anchors 703*a*, 703*b* is both inwards in the x-direction (in the direction of the closure force) and outwards in the y-direction (opposite the direction of the closure force). Thus, a smaller $f_1$ is preferable in these regions to provide more "play" between the anchor elements and the surrounding tissue. Alternatively, the wound closure device is configured so that it does not elongate, but rather does not change its length along the long axis 720.

The variation in the force profile around the periphery of the wound closure device can be achieved in a variety of ways, such as varying the spacing/density of the tissue anchors, the types of anchors, length of anchors, etc. For example, in FIGS. 9A and 9B, anchors 701*a*, 701*b* are longer and penetrate deeper into the tissue compared to anchors 703*a*, 703*b*. The force profile can also be varied by controlling the vacuum force distribution in the filler material, such as by varying the pore size and/or pore density of the filler.

On one embodiment, a method of fabricating a wound closure device of the invention includes forming a stabilizing endoskeleton of rigid or semi-rigid material and forming a collapsible filler material over the endoskeleton. The stabilizing endoskeleton can be formed using a molding process, and can be molded as an integral unit or in one or more components that are then assembled to form the endoskeleton. Different components of the endoskeleton can have different thicknesses and/or degrees of rigidity to provide varying levels of rigidity and flexibility along different directions. The endoskeleton can be assembled by joining components, such as by using a suitable adhesive or other joining process. In certain embodiments, at least some of the components can be assembled to provide articulating joints. In preferred embodiments, the filler material is formed by mixing together appropriate metered amounts of constituent substances, (e.g., isocyanates, polyols, catalysts, surfactants, blowing agents and the like in the case of polyurethane foam), dispensing the reacting mixture into a mold, and then curing and demolding the material. Optionally, the material can then be cut or trimmed to the finished shape. In preferred embodiments, the endoskeleton support structure is assembled and placed into the mold, and the filler material is molded around the endoskeleton. An example of a biodegradable foam product suitable for the present wound closure device, and methods of fabricating such a foam, is described in U.S. Published Application No. 2009/0093550 to Rolfes et al., the entire contents of which are incorporated herein by reference.

Figure 10:
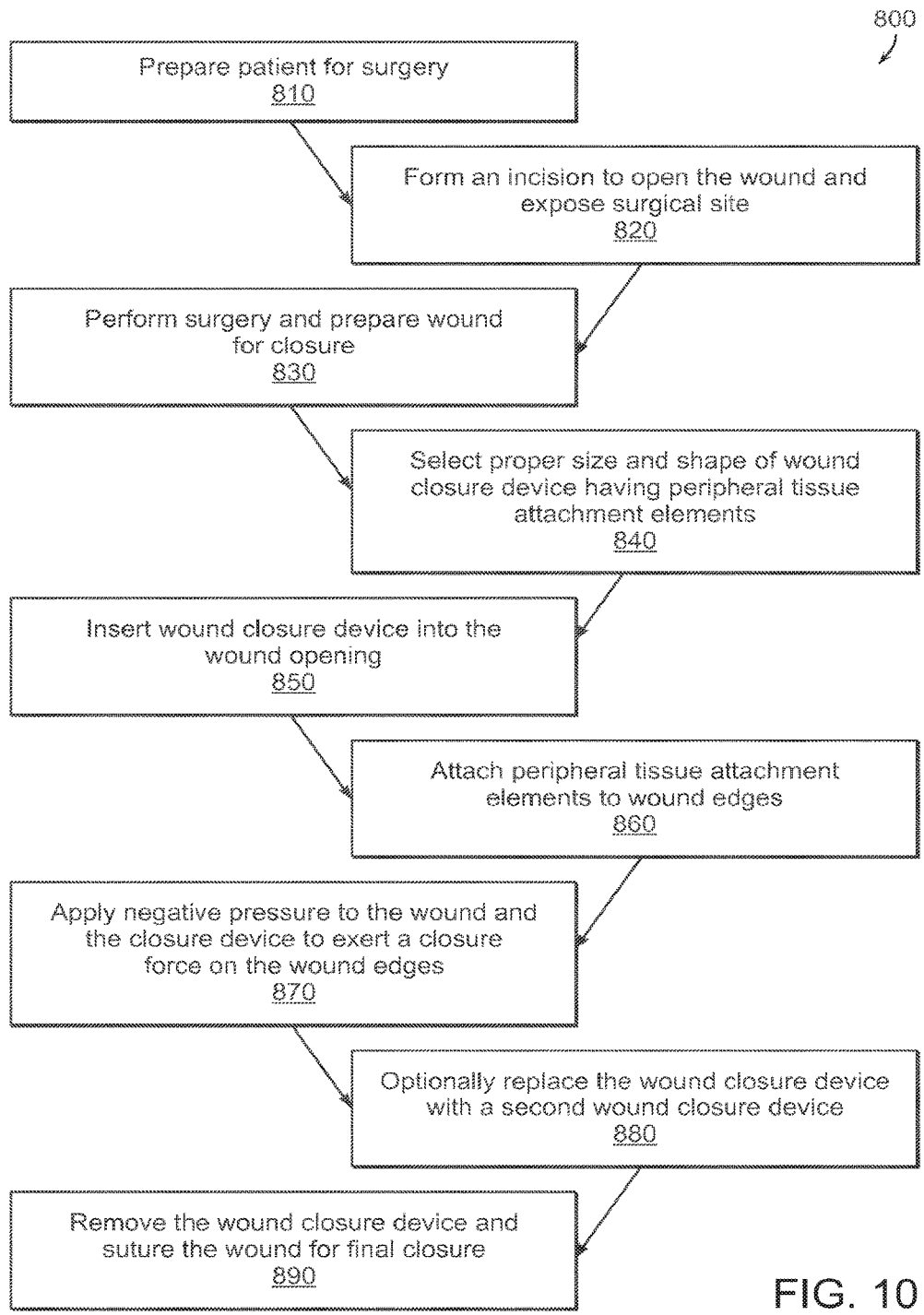
FIG. 10 schematically illustrates a process of using a wound closure device in accordance with the invention.

A method of performing a surgical procedure 800 using a wound closure device in accordance with preferred embodiments of the invention as illustrated in FIG. 10. After preparation 800 of the patient for surgery, an incision is made 820 to expose the surgical site, typically in the abdomen. After the procedure is performed, the wound is prepared 830 for closure. The proper size and shape of the wound closure device is selected 840 with the peripheral tissue attachment members positioned around the circumference or outer wall surface of the device. The device is inserted 850 into the wound and the tissue attachment elements are inserted 860 into the tissue. Negative pressure is then applied 870 to exert a closure force on the wound edges. Depending on the particular application, large wounds may require placement 880 of a smaller second closure after removal of the first larger device. Finally, the device is removed 890 and the wound is closed, typically by suturing.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A method of closing a wound, comprising:
   placing a sliding surface into a wound opening having opposed wound margins;
   inserting a wound closure device into the wound opening over the sliding surface, the wound closure device comprising a wound filler material sized and shaped to fit within the wound opening; and wherein the filler material comprises a stabilizing structure to enable collapse in at least one first direction and inhibit collapse in at least one second direction, the at least one first direction and the at least one second direction extending in a plane through the opposed wound margins, the stabilizing structure inhibiting collapse in a third direction out of the plane and including a plurality of articulating connected elements such that the stabilizing structure collapses in the at least one first direction.

2. The method of claim 1, wherein the stabilizing structure comprises one or more regions of relatively rigid material surrounded by regions of relatively compressible porous material.

3. The method of claim 2, wherein the filler material has length, width and height dimensions, and the stabilizing structure inhibits collapse in the height dimension.

4. The method of claim 1, further comprising collapsing the filler material in at least one first direction to reapproximate the opposed wound margins of the wound.

5. The method of claim 1, further comprising restricting the collapse of the filler material to a plane defined by the wound margins.

6. The method of claim 1, wherein the stabilizing structure comprises an endoskeleton made from comparatively rigid material.

7. The method of claim 6, wherein the endoskeleton comprises a plurality of spaced-apart rigid members forming a cross-hatched configuration.

8. The method of claim 6, further comprising collapsing the filler material in a width dimension and elongating the filler material in a length dimension.

9. The method of claim 6, further comprising inhibiting collapse of the filler material in the third direction with a plurality of rigid members extending in a height dimension.

10. The method of claim 9, wherein at least a portion of the rigid members extending in the height dimension extend around the periphery of the filler material.

11. The method of claim 6, wherein the endoskeleton comprises a network of interconnected rigid members that can articulate at a plurality of joints such that the interconnected members move with respect to one another during collapse of the filler material.

12. The method of claim 6, further comprising inhibiting a tilting or a collapsing motion of the filler material with truss members.

13. The method of claim 1, wherein the filler material has a smooth bottom surface.

14. The method of claim 13, further comprising removing fluid from the wound through micropores formed in the smooth bottom surface.

15. The method of claim 14, further comprising directing a distribution of vacuum force by varying at least one of the size and pore density of the micropores.

16. The method of claim 1, further comprising directing a distribution of vacuum force by varying at least one of a pore size and a pore density within the filler material.

17. The method of claim 1, further comprising removing portions of the filler material to adjust the size of the wound closure device.

18. The method of claim 17, further comprising removing portions of the filler material along pre-determined cleavage lines.

19. The method of claim 1, wherein the inserting step further comprises inserting the wound closure device that includes a peripheral wall.

20. The method of claim 19, further comprising contacting tissue with the peripheral wall, the wall comprising a porous material.

21. The method of claim 20, further comprising removing fluid through the porous material upon application of negative pressure, the porous material comprising a foam that collapses with the stabilizing structure.

22. The method of claim 1, further comprising removing a portion of the wound filler material prior to insertion into the wound.

23. The method of claim 22, wherein the removing step comprises tearing a portion of the wound filler material.

24. The method of claim 22, wherein the removing step comprises cutting a portion of the wound filler material.

25. The method of claim 1, wherein the removing step comprises removing a portion along a cleavage line.

26. The method of claim 22, wherein the removing step comprises removing one or more portions of the wound filler material using one or more cleavage lines within the wound filler material.

27. The method of claim 1, further comprising attaching the wound filler material to a wound margin with a tissue anchor.

28. The method of claim 1, further comprising applying negative pressure to the wound filler material to cause the collapse of the wound filler material.

29. The method of claim 1, further comprising inhibiting collapse of the wound filler material in a vertical direction with rigid vertically extending elements.

30. The method of claim 1, further comprising positioning the wound filler material in an x-y plane between the wound margins of a wound having an oval or circular shape.

31. The method of claim 1, wherein the articulating connected elements have a cross-hatched shape.

32. The method of claim 22, wherein the stabilizing structure includes cleavage lines or points to remove portions of the stabilizing structure.

33. The method of claim 22, wherein the removing step comprises removing portions of a foam material.

34. The method of claim 1, further comprising forming a foam material that is shaped to extend around the stabilizing structure.

35. The method of claim 1, wherein the inserting step further comprises inserting the wound filler material wherein the articulated connected elements are hinged or bend to collapse in the first direction.

36. The method of claim 1, wherein the inserting step further comprises inserting the wound filler material that is positioned over a porous material.

37. The method of claim 1, further comprising inserting the stabilizing structure in an abdominal wound wherein the stabilizing structure has a porous material around and under the stabilizing structure.

38. A method of closing a wound, comprising:
 placing a sliding surface into a wound opening having opposed wound margins;
 inserting a wound closure device into the wound opening over the sliding surface, the wound closure device comprising a wound filler material sized and shaped to fit within the wound opening;
 wherein the filler material comprises a stabilizing structure to enable collapse in at least one first direction and inhibit collapse in at least one second direction, the at least one first direction and the at least one second direction extending in a plane through the opposed wound margins, the stabilizing structure including a plurality of articulating connected elements such that the stabilizing structure collapses in the at least one first direction.

39. The method of claim 38, wherein the wound filler material collapses by sliding over the sliding surface positioned in an abdominal wound.

40. The method of claim 38, further comprising applying negative pressure to the wound such that fluid is removed through pores formed in the sliding surface and a porous material within the wound closure device.

41. The method of claim 38, wherein the stabilizing structure comprises one or more regions of relatively rigid material surrounded by regions of relatively compressible porous material.

42. The method of claim 41, wherein the filler material has length, width and height dimensions, and the stabilizing structure inhibits collapse in the height dimension.

43. The method of claim 38, wherein the stabilizing structure comprises an endoskeleton made from comparatively rigid material.

44. The method of claim 43, wherein the endoskeleton comprises a plurality of spaced-apart rigid members forming a cross-hatched configuration.

45. The method of claim 43, further comprising collapsing the filler material in a width dimension and elongating the filler material in a length dimension.

46. The method of claim 43, further comprising inhibiting collapse of the filler material in a third direction with a plurality of rigid members extending in a height dimension.

47. The method of claim 46, wherein at least a portion of the rigid members extending in the height dimension extend around the periphery of the filler material.

48. The method of claim 43, wherein the endoskeleton comprises a network of interconnected rigid members that can articulate at a plurality of joints such that the interconnected members move with respect to one another during collapse of the filler material.

49. The method of claim 43, further comprising inhibiting a tilting or a collapsing motion of the filler material with truss members.

50. The method of claim 38, wherein the inserting step further comprises inserting the wound closure device that includes a peripheral wall.

51. The method of claim 50, further comprising contacting tissue with the peripheral wall, the wall comprising a porous material.

52. The method of claim 51, further comprising removing fluid through the porous material upon application of negative pressure, the porous material comprising a foam that collapses with the stabilizing structure.

53. A method of closing a wound, comprising:
inserting a wound closure device into a wound opening having opposed wound margins, the wound closure device comprising a wound filler material sized and shaped to fit within the wound opening, the filler material comprising a stabilizing structure to enable collapse in at least one first direction and inhibit collapse in at least one second direction, the at least one first direction and the at least one second direction extending in a plane through the opposed wound margins, the stabilizing structure including a plurality of articulating connected elements such that the stabilizing structure collapses in the at least one first direction, wherein a foam material is shaped to extend around the stabilizing structure; and
applying negative pressure to the wound closure device.

54. The method of claim 53, wherein the filler material has a smooth bottom surface.

55. The method of claim 54, further comprising removing fluid from the wound through micropores formed in the smooth bottom surface.

56. The method of claim 53, further comprising placing a sliding surface beneath the wound closure device.

57. The method of claim 53, wherein the stabilizing structure comprises one or more regions of relatively rigid material surrounded by regions of relatively compressible porous material.

58. The method of claim 57, wherein the filler material has length, width and height dimensions, and the stabilizing structure inhibits collapse in the height dimension.

59. The method of claim 53, wherein the stabilizing structure comprises an endoskeleton made from comparatively rigid material.

60. The method of claim 59, wherein the endoskeleton comprises a plurality of spaced-apart rigid members forming a cross-hatched configuration.

61. The method of claim 59, further comprising collapsing the filler material in a width dimension and elongating the filler material in a length dimension.

62. The method of claim 59, further comprising inhibiting collapse of the filler material in a third direction with a plurality of rigid members extending in a height dimension.

63. The method of claim 62, wherein at least a portion of the rigid members extending in the height dimension extend around the periphery of the filler material.

64. The method of claim 59, wherein the endoskeleton comprises a network of interconnected rigid members that can articulate at a plurality of joints such that the interconnected members move with respect to one another during collapse of the filler material.

65. The method of claim 59, further comprising inhibiting a tilting or a collapsing motion of the filler material with truss members.

66. The method of claim 53, wherein the inserting step further comprises inserting the wound closure device that includes a peripheral wall.

67. The method of claim 66, further comprising contacting tissue with the peripheral wall, the wall comprising a porous material.

68. The method of claim 67, further comprising removing fluid through the porous material upon application of negative pressure, the porous material comprising a foam that collapses with the stabilizing structure.

* * * * *